United States Patent [19]

Enari et al.

[11] Patent Number: 5,108,925
[45] Date of Patent: Apr. 28, 1992

[54] PROCESS FOR ACCELERATED BEER PRODUCTION BY INTEGRATIVE EXPRESSION IN THE PGK1 OR ADC1 GENES

[75] Inventors: Tor-Magnus Enari, Espoo; Matti J. Nikkola, Ilmajoki; Maija-Liisa A. Suthko, Espoo; Merja E. Penttilä; Päivi M. Lehtovaara-Helenius, both of Helsinki, all of Finland

[73] Assignee: Oy Panimolaboratorio - Bryggerilaboratorium Ab, Helsinki, Finland

[21] Appl. No.: 324,693

[22] Filed: Mar. 17, 1989

Related U.S. Application Data

[63] Continuation-in-part of Ser. No. 44,244, Apr. 30, 1987, abandoned.

[30] Foreign Application Priority Data

Mar. 17, 1987 [FI] Finland .................................. 871163
Mar. 17, 1988 [FI] Finland .................................. 881279

[51] Int. Cl.⁵ ................... C12C 11/00; C12C 11/04; C12N 1/18
[52] U.S. Cl. ...................................... 435/256; 426/11; 426/16; 435/172.3; 435/232; 435/255; 435/325.1; 935/37; 935/56; 935/69
[58] Field of Search .................... 435/282, 172.3, 256, 435/255, 320, 828, 940, 312.1, 161; 935/37, 56, 69; 426/11, 16; 536/27

[56] References Cited

U.S. PATENT DOCUMENTS 4,895,802  1/1992  Sone et al. .................... 435/172.3

FOREIGN PATENT DOCUMENTS 0228009  7/1987  European Pat. Off. .
84/02921  8/1984  PCT Int'l Appl. .

OTHER PUBLICATIONS

M. L. Suihko et al. EBC Congress Proceedings, pp. 483–490 (1989).
Sone et al., Journal of Biotechnology, 5, pp. 87–91 (1987).
Godtfredsen et al., Carlsberg Res. Commun.. vol. 49, pp. 69–74 (1984).
Rudolph et al., Gene, 36, pp. 87–95 (1985).
McGraw III, Analytical Biochemistry, 143, pp. 298–303 (1984).
Sone et al., Appl. Environ. Microbiol., 54, 38–42 (Jan. 1988).

*Primary Examiner*—Robin L. Teskin
*Attorney, Agent, or Firm*—Birch, Stewart, Kolasch & Birch

[57] ABSTRACT

The present invention describes a shortened process for the production of beer, brewer's yeast strains having α-acetolactate decarboxylase activity (EC 4.1.1.5.), the method for the construction of such yeast strains and the recombinant DNA cloning vectors used. The method involves integrating the α-acetolactate decarboxylase gene into the ADC1 or PGK1 gene.

16 Claims, 36 Drawing Sheets

A. The spontaneous decarboxylation of α-acetolactate to diacetyl in beer.
B. The enzymatic reduction of diacetyl to acetoin by yeast cells during secondary fermentation.
C. The decarboxylation of α-acetolactate directly to acetoin catalyzed by α-ALDC during primary fermentation.

FIG. 3(1).

```
                                                                    ┐
←──────────── Bluescribe M13 + ────────────────────
                              EcoRI SacI Asp718    │
        10        20        30        40        50 │       60
GCCAGTGAATTGTAATACGACTCACTATAGGGCGAATTCGAGCTCGGTACCCGGGGATCG 70        80        90       100       110       120
TGGGCCGCCCGAGTGAAGTTCCGCGCCTCGGCAACGGCGACAAAATAACGTAAATAGCGA 130       140       150       160       170       180
AGTTCCATATCGTAAACGTCTCAAACCAGCATGGATTCTATATTGGAACTGAGAGCTGAA 190       200       210       220       230       240
TCGGGTCAATATTTATTTAATCTTTCTTATATTTGTTGAACGAGGAAGTGGATTGTGAAT
                                                        ValAsn 250       260       270       280       290       300
CATTATCCTGAATGCACCTGCCAGGAGAGCCTGTGCGAAACCGTACGCGGCTTCTCCGCC
HisTyrProGluCysThrCysGlnGluSerLeuCysGluThrValArgGlyPheSerAla 310       320       330       340       350       360
CACCACCCTGATAGCGTTATCTATCAGACCTCTCTGATGAGCGCGCTGCTGAGCGGGGTC
HisHisProAspSerValIleTyrGlnThrSerLeuMetSerAlaLeuLeuSerGlyVal 370       380       390       400       410       420
TATGAGGGTAGCACCACCATCGCCGACCTGCTGACCCACGGCGACTTCGGTCTCGGCACC
TyrGluGlySerThrThrIleAlaAspLeuLeuThrHisGlyAspPheGlyLeuGlyThr 430       440       450       460       470       480
TTTAACGAACTCGATGGCGAACTGATTGCCTTTAGCAGCGAGGTCTACCAGCTGCGCGCT
PheAsnGluLeuAspGlyGluLeuIleAlaPheSerSerGluValTyrGlnLeuArgAla 490       500       510       520       530       540
GACGGCAGCGCGCGTAAAGCCCGGGCGGATCAAAAAACGCCCTTCGCGGTGATGACCTGG
AspGlySerAlaArgLysAlaArgAlaAspGlnLysThrProPheAlaValMetThrTrp 550       560       570       580       590       600
TTCAGACCGCAGTACCGTAAAACCTTTGACCACCCGGTCAGCCGCCAGCAGCTGCACGAC
PheArgProGlnTyrArgLysThrPheAspHisProValSerArgGlnGlnLeuHisAsp 610       620       630       640       650       660
GTTATCGACCAGCAAATCCCCTCCGATAACCTGTTCTGCGCCCTGCATATTGATGGTCAC
ValIleAspGlnGlnIleProSerAspAsnLeuPheCysAlaLeuHisIleAspGlyHis 670       680       690       700       710       720
TTTCGCCACGCCCACACCCGCACCGTGCCGCGGCAGACGCCGCCCTATCGGGCGATGACC
PheArgHisAlaHisThrArgThrValProArgGlnThrProProTyrArgAlaMetThr
```

FIG. 3(2).

```
         730       740       750       760       770       780
GACGTGCTCGATGACCAGCCGGTTTTCCGCTTCAACCAGCGCAAGGGGACGCTGGTCGGC
AspValLeuAspAspGlnProValPheArgPheAsnGlnArgLysGlyThrLeuValGly 790       800       810       820       830       840
TTTCGCACCCCGCAGCATATGCAGGGCCTTAACGTTGCCGGCTACCACGAGCACTTTATT
PheArgThrProGlnHisMetGlnGlyLeuAsnValAlaGlyTyrHisGluHisPheIle 850       860       870       880       890       900
ACCGACGATCGCCAGGGCGGCGGCCATCTGCTGGACTACCAGCTCGATAGCGGCGTGCTG
ThrAspAspArgGlnGlyGlyGlyHisLeuLeuAspTyrGlnLeuAspSerGlyValLeu 910       920       930       940       950       960
ACCTTCGGCGAGATCCACAAGCTGATGATTGACCTCCCGGCCGACAGCGCTTTCCTGCAG
ThrPheGlyGluIleHisLysLeuMetIleAspLeuProAlaAspSerAlaPheLeuGln 970       980       990      1000      1010      1020
GCCGACCTGCATCCTGACAATCTCGATGCCGCTATTCGTGCGGTAGAAAACTAAGGAGCT
AlaAspLeuHisProAspAsnLeuAspAlaAlaIleArgAlaValGluAsnEnd 1030      1040      1050      1060      1070      1080
TCAGATGGACAAACCGCGTCACGAACGTCAATGGGCCCACGGTGCCGACTTAATCGTCAG 1090      1100      1110      1120      1130      1140
CCAGCTTGAGGCCCAGGGCGTACGCCAGGTCTTCGGCATCCCCGGTGCCAAAATCGACAA
                                    HindIII
        1150      1160      1170      1180
GGTGTTTGATTCCCTCCTCGACTCCTCAAGCTTTTGTTCCC
                                  └─Bluescribe M13 + ─────────>
``` oligonucleotide "ald-loop"

FIG. 6(1).

```
         10        20        30        40        50        60
ATTGGAACTCTCTGCTGAATCGGGTCAACATTTATTAAACCTTTATAAATAAAGTTGAAG 70        80        90       100       110       120
AGGACGGGCATGATGATGCATTCATCTGCATGCGACTGTGAGGCGAGTTTATGCGAGACC
           MetMetMetHisSerSerAlaCysAspCysGluAlaSerLeuCysGluThr 130       140       150       160       170       180
CTGCGTGGGTTCTCGGCTCAGCATCCTGACAGCGTGATCTATCAGACATCGCTAATGAGC
LeuArgGlyPheSerAlaGlnHisProAspSerValIleTyrGlnThrSerLeuMetSer 190       200       210       220       230       240
GCCCTGCTAAGCGGTGTCTACGTAGGGGAGACGACGATCGCCGACCTGCTGGCACACGGT
AlaLeuLeuSerGlyValTyrValGlyGluThrThrIleAlaAspLeuLeuAlaHisGly 250       260       270       280       290       300
GATTTTGGTCTCGGCACCTTTAACGAGCTGGACGGTGAAATGATTGCCTTCAGCAGCCAG
AspPheGlyLeuGlyThrPheAsnGluLeuAspGlyGluMetIleAlaPheSerSerGln 310       320       330       340       350       360
GTGTACCAGCTGCGCGCCGACGGCAGCGCCCGCGCCGCGAAGCCGGAGCAAAAAACGCCG
ValTyrGlnLeuArgAlaAspGlySerAlaArgAlaAlaLysProGluGlnLysThrPro 370       380       390       400       410       420
TTCGCGGTGATGACCTGGTTCCAGCCGCAGTACCGCAAAACCTTTAACGGTCCGGTCAGC
PheAlaValMetThrTrpPheGlnProGlnTyrArgLysThrPheAsnGlyProValSer 430       440       450       460       470       480
CGTCAGCAGATCCACGACGTGATCGACCAGCAGATCCCCTCCGATAACCTGTTCTGCGTG
ArgGlnGlnIleHisAspValIleAspGlnGlnIleProSerAspAsnLeuPheCysVal 490       500       510       520       530       540
CGCATCGATGGCAACTTCCGCCATGCGCATACCCGCACCGTTCCGCGCCAGACGCCGCCG
ArgIleAspGlyAsnPheArgHisAlaHisThrArgThrValProArgGlnThrProPro 550       560       570       580       590       600
TACCGGGCAATGACCGACGTGCTGGACGACCAGCCGGTGTTCCGCTTTAACCAACGCGAG
TyrArgAlaMetThrAspValLeuAspAspGlnProValPheArgPheAsnGlnArgGlu 610       620       630       640       650       660
GGCGTGCTGGTCGGGTTCCGCACCCCGCAGCATATGCAGGGCATCAACGTGGCGGGCTAT
GlyValLeuValGlyPheArgThrProGlnHisMetGlnGlyIleAsnValAlaGlyTyr 670       680       690       700       710       720
CACGAGCACTTTATCACCGACGACCGTCAGGGCGGCGGCCATCTGCTCGACTATCAGCTG
HisGluHisPheIleThrAspAspArgGlnGlyGlyGlyHisLeuLeuAspTyrGlnLeu 730       740       750       760       770       780
GAGAGCGGCGTGCTCACCTTTGGCGAAATCCACAAGCTGATGATTGACCTGCCCGCCGAC
GluSerGlyValLeuThrPheGlyGluIleHisLysLeuMetIleAspLeuProAlaAsp
```

FIG. 6(2).

```
        790       800       810       820       830       840
AGCGCGTTTTTACAGGCCAACCTGCACCCCAGCAACCTTGATGCGGCTATCCGCGCCGTC
SerAlaPheLeuGlnAlaAsnLeuHisProSerAsnLeuAspAlaAlaIleArgAlaVal 850       860       870       880       890       900
GAAAACTAACAGGAGAACTACCGTGAACAGTGAGAAACAGTCACGTCAGTGGGCGCACGG
GluAsn 910       920       930       940       950    Bam HI
CGCCGATATGGTTGTCGGCCAGCTGGAAGCGCAGGGTGTGAAGCAGGTGTTCGGGATCC
``` oligonucleotide "eld-loop"

FIG. 13(2).
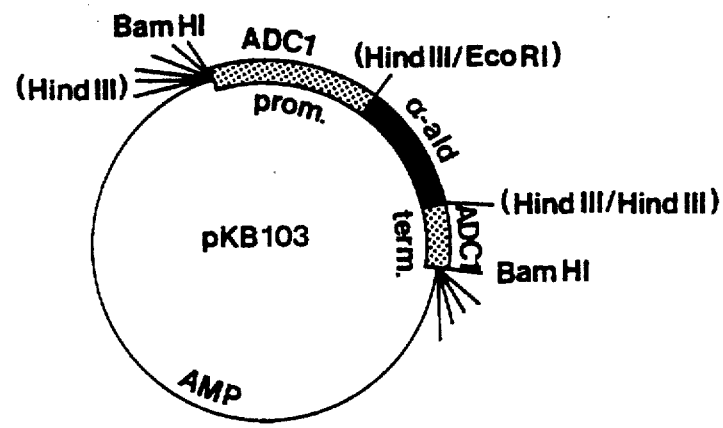
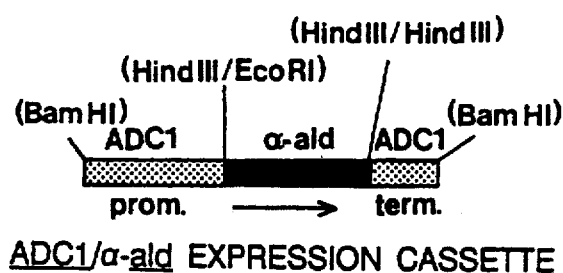
ADC1/α-ald EXPRESSION CASSETTE
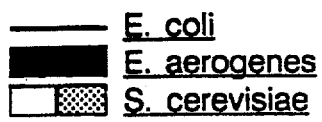

Control strain o, △, □
Strain VTT-A-87083 ●, ▲, ■

Control strain ○, △, □
Strain VTT-A-88087 ●, ▲, ■

Control strain o, △, □
Strain VTT-A-87076 ●, ▲, ■

Control strain ○, △, □
Strain VTT-A-88088 ●, ▲, ■

FIG. 17.

| Analysis | | Control | VTT-A-87083 | VTT-A-87076 | Control | VTT-A-88087 | VTT-A-88088 |
|---|---|---|---|---|---|---|---|
| | | | | Yeast strain used | | | |
| Alcohol | % (w/w) | 3.65 | 3.55 | 3.60 | 3.75 | 3.60 | 3.70 |
| Apparent extract | % (w/w) | 1.85 | 1.80 | 1.75 | 1.55 | 1.60 | 1.60 |
| Real extract | % (w/w) | 3.50 | 3.40 | 3.40 | 3.30 | 3.30 | 3.30 |
| Original gravity | % (w/w) | 10.6 | 10.4 | 10.5 | 10.6 | 10.4 | 10.5 |
| Apparent attenuation | % | 82.5 | 82.5 | 83.5 | 85.5 | 84.5 | 85.0 |
| Real attenuation | % | 67.0 | 67.0 | 67.5 | 69.0 | 68.5 | 69.0 |
| Colour | °EBU | 8.5 | 8.5 | 9.0 | 8.5 | 9.0 | 9.0 |
| Bitterness | EBU | 21 | 22 | 19 | 19 | 21 | 21 |
| Turbidity | FU | 0.5 | 0.3 | 0.3 | 0.3 | 0.5 | 0.4 |
| Chemical stability | FU | >12 | 7.9 | >12 | >12 | 5.7 | 11.1 |
| Foam stability | s | 261 | 262 | 249 | 228 | 241 | 241 |
| pH | | 4.3 | 4.2 | 4.2 | 4.3 | 4.2 | 4.2 |
| Flavour compounds: | | | | | | | |
| Ethyl acetate | mg/l | 13.3 | 10.2 | 19.8 | 16.8 | 13.1 | 13.5 |
| n-Propanol | mg/l | 11.2 | 11.2 | 12.4 | 10.4 | 11.5 | 11.6 |
| i-Amyl acetate | mg/l | 1.0 | 0.7 | 2.3 | 1.3 | 0.9 | 1.0 |
| i-Butanol | mg/l | 10.2 | 8.4 | 12.5 | 9.7 | 8.2 | 10.1 |
| Ethyl caproate | mg/l | 0.2 | <0.05 | <0.05 | 0.2 | 0.2 | 0.2 |
| 3-methylbutanol | mg/l | 14.3 | 13.6 | 18.4 | 14.4 | 12.3 | 14.7 |
| 2-methylbutanol | mg/l | 40.6 | 41.7 | 51.7 | 36.5 | 36.8 | 41.8 |
| Total diacetyl | mg/l | 0.019 | 0.004 | 0.006 | 0.030 | 0.015 | 0.024 |
| Total VDK | mg/l | 0.033 | 0.009 | 0.020 | 0.053 | 0.034 | 0.045 |
| Taste evaluation* | | 4 | 3 | 4 | 3 | 3 | 3 |

*Scores: 5 = Excellent   4 = Good   3 = Fairly good   2 = Poor   1 = Unacceptable Control strain  o, △, □
Strain VTT-A-88085  ●, ▲, ■

Control strain ○, △, □
Strain VTT-A-88086 ●, ▲, ■

Control strain o, △, □
Strain VTT-A-88090 ●, ▲, ■

FIG. 19.

| Analysis | | Yeast strain used | | | | | | |
|---|---|---|---|---|---|---|---|---|
| | | Control | VTT-A-88085 | VTT-A-88086 | Control | VTT-A-88089 | VTT-A-88090 |
| Alcohol | % (w/w) | 3.15 | 3.15 | 3.15 | 3.45 | 3.35 | 3.45 |
| Apparent extract | % (w/w) | 2.80 | 2.85 | 2.90 | 2.35 | 2.25 | 2.40 |
| Real extract | % (w/w) | 4.25 | 4.30 | 4.35 | 3.95 | 3.95 | 3.85 |
| Original gravity | % (w/w) | 10.5 | 10.5 | 10.6 | 10.7 | 10.5 | 10.6 |
| Apparent attenuation | % | 73.0 | 73.0 | 72.5 | 78.0 | 77.0 | 78.5 |
| Real attenuation | % | 59.5 | 59.0 | 59.0 | 63.5 | 62.5 | 63.5 |
| Colour | °EBU | 7.5 | 8.0 | 7.8 | 8.2 | 9.1 | 8.5 |
| Bitterness | EBU | 19 | 19 | 21 | 21 | 20 | 16 |
| Turbidity | FU | 0.2 | 0.2 | 0.2 | 0.3 | 0.3 | 0.3 |
| Chemical stability | FU | 1.5 | 3.8 | 4.7 | >12 | 2.8 | >12 |
| Foam stability | s | 271 | 280 | 263 | 276 | 283 | 284 |
| pH | | 4.2 | 4.1 | 4.1 | 4.1 | 4.1 | 4.3 |
| Flavour compounds: | | | | | | | |
| Ethyl acetate | mg/l | 11.9 | 8.6 | 9.5 | 11.3 | 8.0 | 8.0 |
| n-Propanol | mg/l | 9.9 | 10.5 | 10.6 | 10.4 | 11.2 | 10.5 |
| i-Amyl acetate | mg/l | 1.4 | 0.7 | 0.8 | 0.5 | 0.5 | 0.5 |
| i-Butanol | mg/l | 8.8 | 10.3 | 11.5 | 9.1 | 7.7 | 6.5 |
| Ethyl caproate | mg/l | 0.2 | 0.1 | 0.1 | 0.1 | 0.1 | 0.1 |
| 3-methylbutanol | mg/l | 14.4 | 15.4 | 15.4 | 12.9 | 11.5 | 10.6 |
| 2-methylbutanol | mg/l | 40.4 | 53.5 | 51.4 | 34.4 | 35.7 | 31.8 |
| Total diacetyl | mg/l | 0.011 | 0.008 | 0.011 | 0.017 | 0.007 | 0.020 |
| Total VDK | mg/l | 0.015 | 0.016 | 0.018 | 0.021 | 0.011 | 0.024 |
| Taste evaluation* | | 3 | 3 | 3 | 3 | 3 | 2 |

*Scores: 5 = Excellent  4 = Good  3 = Fairly good  2 = Poor  1 = Unacceptable

PROCESS FOR ACCELERATED BEER PRODUCTION BY INTEGRATIVE EXPRESSION IN THE PGK1 OR ADC1 GENES

CROSS-REFERENCE TO RELATED APPLICATIONS

This application is a continuation-in-part of copending application Ser. No. 07/044,244 filed on Apr. 30, 1987 now abandoned.

BACKGROUND OF THE INVENTION

A. Field of the Invention

The present invention describes a shortened process for production of beer, brewer's yeast strains having α-acetolactate decarboxylase activity (EC 4.1.1.5.) (later α-ALDC), the method for the construction of such yeast strains and the recombinant DNA cloning vectors used.

The conventional brewing process can be shortened by accelerating either the primary fermentation or the secondary fermentation, or by producing beer in a continuous process. Of the different stages in the production of beer, the secondary fermentation, which is required for flavour maturation, takes the longest time (2-3 weeks) and requires much refrigerated space. Accelerating the costly flavour maturation is therefore more important than the speeding up of other stages of the process. A brewer's yeast capable of accelerated flavour maturation would have considerable economic value in the production of beer.

During the primary fermentation, yeast forms α-acetolactate, which is an intermediate in the biosynthesis of valine. Part of the α-acetolactate, not used in the synthesis of valine, leaks out of the yeast cell to the fermenting beer. In the beer, diacetyl is formed from this α-acetolactate by a spontaneous reaction. During secondary fermentation, diacetyl is enzymatically reduced to acetoin by the yeast (FIG. 1).

The degree of maturity of beer is determined in practice by its content of diacetyl, which is a typical aroma compound of butter. The taste and smell of diacetyl can be detected at a very low level and most people find it very obnoxious in beer. In light lager beers, the taste threshold value of diacetyl is between 0.02-0.05 mg/l. The taste threshold value of acetoin in beer is markedly higher (50 mg/l) than that of diacetyl.

B. Description of the Prior Art

Certain taxa of bacteria, e.g. enterobacteria (Aerobacter, Klebsiella, Enterobacter) and the Lactobacillus, Bacillus and Streptococcus bacteria used traditionally in the food industry have been found to possess the α-ALDC enzyme (EC 4.1.1.5.), which catalyzes the decarboxylation of α-acetolactate into acetoin (Godtfredsen et al., 1983). Klebsiella has been shown to be one of the best α-ALDC producers of the bacteria studied. The enzyme has not been found in organisms taxonomically higher than bacteria.

In laboratory experiments α-ALDC enzyme preparations have been added to freshly fermented beer, which resulted in the removal of diacetyl and its precursor from the beer within 24 h (Godtfredsen and Ottesen, 1982). Consequently, the time required for the maturation of beer was shortened. The quality of beer matured using α-ALDC was not found to be different from that of beer matured in the traditional way. It is to be noted that the use of additives in the production of beer is prohibited by food regulations in some countries. In addition, the commercial enzyme preparations are unspecific and thus contain also other enzyme activities as impurities. The addition of enzyme during the brewing process also increases the risk of contamination.

It is possible that accelerated secondary fermentation could be achieved not only by adding α-ALDC enzyme to young beer, but also by isolating the gene coding for this enzyme (later α-ald) from a suitable donor organism and expressing this gene in yeast. A yeast expressing this gene will produce the enzyme α-ALDC during primary fermentation and excess α-acetolactate would be decarboxylated directly to acetoin. Thus the addition of enzyme preparations to beer would become unnecessary. Using a brewer's yeast which carries only the specific gene would thus result in a rapid and clean process with no additives required.

The gene coding for α-ALDC has been isolated from *Enterobacter aerogenes* strain IFO 13534 (Sone et al., 1987). The gene was shown to be present on a 1.7 kb DNA-fragment but the localization of the gene in this DNA fragment was not given nor was its nucleotide sequence determined. In addition, no description of the methods used to express this gene in yeast was provided.

Although some bacterial DNA sequences carrying a coding region for a protein e.g. β-lactamase can be expressed in yeast, the expression is in most of the cases insufficient or no expression is observed. To be efficiently expressed in yeast, the foreign gene has to be coupled to yeast regulatory sequences (promoter and terminator). In order to do this, the nucleotide sequence of the gene must be determined and the region coding for the protein must be exactly known.

Unlike yeast, many bacteria can utilize GTG in addition to ATG as a start codon for protein synthesis. Thus, although the gene would be coupled to yeast regulatory sequences, the authentic protein would not be produced in these cases. When the N-terminal amino acid sequence of the protein is not known, as is the case with the α-ALDC enzymes, the correct N-terminus cannot always be identified from the nucleotide sequence. This is even more difficult if both GTG and ATG can represent a start codon. If DNA sequences of the gene are available from other closely related organisms, homology of the sequences facilitates the localization of the coding region. In any case, the only way to show that a piece of DNA is functional in yeast, is to demonstrate corresponding enzyme activity in yeast cells transformed with this DNA molecule.

When a protein coding region is correctly coupled to yeast regulatory sequences expression of the foreign gene in yeast is sometimes obtained and the corresponding protein is made in some form. However, there is no way to predict the exact production level of the protein. This depends, for instance, on the promoter used, the exact expression construction made, and the copy number of the gene in the transformant. It also depends on the precise nature of each protein. Consequently, some heterologous proteins cannot be produced in active form in yeast (Hollenberg, 1987), some are unstable due to cytoplasmic proteolysis (Stepien et al., 1983; Urdea et al., 1983) and some are produced at a very much lower level than expected (Mellor et al., 1983). Even a low level of expression can be harmful or even toxic to the cell and production of a foreign protein can lead to a very much reduced growth rate of the yeast (Kingsman et al., 1985). When genes involved in the house keeping activities of the cell, like the α-ald gene involved in the leucine-valine pathway, are expressed, it is impossible to predict the changes caused in the yeast metabolism. E.g. the formation of fusel oils, the main flavour compounds of beer, is linked to the amino acid metabolism of brewer's yeast cells.

Alteration of the amounts of different higher alcohols (fusel oils) has serious effects on the taste of beer. As important, since the enzyme α-ALDC effectively removes α-acetolactate from the cellular pool, is that overproduction of the enzyme would make the yeast auxotrophic, in that it would require the addition of isoleucine and valine to the wort. This would naturally disturb the growth of the yeast and thus alter the flavour and alcohol content of the beer. This type of yeast would therefore be useless for production of beer.

In brewing, the character and quality of the final product, beer, is directly dependent on the growth and metabolism of the yeast strain used in the process. Slight changes can dramatically affect the amount of numerous flavour compounds as well as alcohol produced by the brewer's yeast or cause technical problems in the process. The expression of a foreign gene has to be fine-tuned so that the brewing properties of the strain are not altered.

Since the brewer's yeast is a food microbe, it is important that the yeast does not contain any heterologous DNA other than the coding region for the α-ald gene and that the rearrangements caused to the yeast genome are minimal. One way to achieve this is to integrate the gene to the yeast chromosome. The place of integration has to be considered since integration to some chromosomal loci might cause reduced growth rate or instability of the integrated DNA (Penttilä et al., 1987). Stability of the foreign DNA in the strain is important especially in brewing where the yeast is normally recycled in several successive fermentations and where no additional selection pressure can be applied.

The function of the gene, its stability and the effects of the enzyme produced have to be shown in a brewer's yeast strain used normally for production of beer and in conditions (pilot scale) which correspond closely to the actual full scale process. Only these results permit the demonstration that the brewer's yeast producing α-ALDC can be used for beer production.

SUMMARY OF THE INVENTION

The present invention describes the isolation of the α-ald gene from two different bacteria, the characterization of the genes, the transfer and expression of the genes in brewer's yeast, the brewing properties of the recombinant brewer's yeasts and their effect on the brewing process and the quality of beer.

The level of expression should be optimal with regard to the whole brewing process. With the cloning vectors and the yeast strains described in this invention, an optimal solution has been found.

The α-ald gene is coupled to yeast regulatory regions (promoter and terminator) which are active during the fermentation and this construction is transferred to a brewer's yeast. The resulting brewer's yeast produces α-ALDC during the primary fermentation. The enzyme resides in the cytoplasm of the yeast and decarboxylates α-acetolactate to acetoin. Secondary fermentation is markedly shortened or completely unnecessary.

Since brewer's yeast is a food microbe, it is important that the yeast chromosome will only contain the α-ald gene together with the yeast regulatory regions and no other heterologous DNA sequences. This can be achieved by using DNA molecules of two types in the yeast transformation, the one being the proper DNA fragment containing the α-ald gene to be integrated into the chromosome, and the other an autonomously replicating plasmid molecule containing the selection marker needed for selection of the transformants.

A certain proportion of the yeast clones harboring the selection plasmid, will also have received the α-ald gene, which has become a stable part of the yeast chromosome. By growing the yeast clone under non-selective conditions, it can be cured of the plasmid carrying the marker gene. The final result of the transformation will be a strain with no foreign DNA other than that of the α-ald structural gene.

In the method according to the present invention, to construct yeast strains suitable for accelerated brewing, the gene coding for α-ALDC enzyme is transferred from a bacterium containing this gene (e.g. *Aerobacter aerogenes*, *Enterobacter aerogenes*, *Lactobacillus casei*, *Bacillus brevis*, *Bacillus licheniformis*) to yeast using recombinant-DNA-technology.

The yeast receiving the gene is a lager brewer's yeast strain of *Saccharomyces cerevisiae* (ex. *S. carlsbergensis*, ex. *S. uvarum*) e.g. one of the following: VTT-A-62007, VTT-A-63015, VTT-A-62016, VTT-A-66023, VTT-A-66024, VTT-A-82064 or VTT-A-85072.

The α-ald genes of the donor bacteria are isolated from the chromosomal DNA of the bacteria using e.g. *Escherichia coli* bacteria as a host, and the nucleotide sequences of the genes are determined.

It is thus an object of this invention to provide specific α-ald genes.

The α-ald genes are transferred to yeast coupled to gene regulatory regions isolated from yeast, which regulate the expression of the gene in the yeast cell in brewing conditions. Suitable yeast gene regulatory regions are e.g. the promoter and terminator regions of the yeast phosphoglycerokinase gene (PGK1) (Mellor et al., 1983) or the corresponding regions of the yeast alcohol dehydrogenase gene (ADC1), iso-1-cytochrome c gene (CYC1) (Cantwell et al., 1986) or the enolase gene (ENO1) (Innis et al., 1985).

Thus it is another object of this invention to provide specific yeast vectors and expression cassettes containing the α-ald gene.

The genes are transferred to yeast on an autonomously replicating plasmid or by integrating it to the yeast chromosome by using e.g. the co-transformation method (Penttilä et al., 1987) using as the selection marker a yeast dominance marker, e.g. the yeast CUP1 copper resistance gene in the yeast plasmid pET13:1 (Henderson et al., 1985). As a dominance marker also e.g. genes which encode resistance to chloramphenicol or G418 can be used (Knowles and Tubb, 1987). After the selection of transformants the yeast cells are allowed to be cured of the plasmid, which is not needed any longer, and only the transferred gene will remain in the yeast cells and has become a part of the chromosome (Penttilä et al., 1987). Also, the marker gene needed can be first integrated to the yeast genome and later removed from the yeast cell by in vivo-recombination (Yocum, 1986).

It is still another object of the present invention to provide yeast strains, which contain a DNA fragment coding for an enzyme having α-ALDC (EC 4.1.1.5.) activity and which are thus able to produce α-ALDC during primary fermentation.

The α-ald gene integrated into the yeast chromosome is expressed in the yeast and active enzyme is produced, whereby all or most of the extra α-acetolactate is directly converted into acetoin and the time required for flavour maturation is markedly shortened.

The expression of the genes and the activity of the gene products are detected by measuring the α-ALDC activity from the cell extract of the yeast containing the gene. The conversion of the added α-acetolactate directly into acetoin is confirmed by gas chromatography.

The brewing properties of the recombinant brewer's yeasts and their effect on the brewing process are tested in pilot scale brewing (à 50 l). During the primary fermentation yeast growth and flocculation, decrease in apparent extract and formation of total diacetyl (free diacetyl and α-acetolactate) are followed. If needed, the primary fermentation is followed by a short secondary fermentation or the process continues directly to downstream process: stabilization, filtration, bottling and pasteurization. The finished beers are analyzed for apparent and real extract, apparent and real attenuation, original gravity, alcohol content, pH, colour, bitter substances, turbidity, chemical stability, foam stability, total vicinal diketones (free diacetyl and 2,3-pentanedione as well as their precursors, α-acetolactate and α-acetohydroxybutyrate) (later VDK) and the main flavour compounds (fusel oils and esters). The beers are also tasted by the tasting panel and evaluated using the international flavour terms.

Thus, this invention describes an improvement to the present process for the production of beer in which the secondary fermentation is markedly shortened or not required at all.

BRIEF DESCRIPTION OF THE DRAWINGS

FIG. 3 shows the nucleotide sequence, and the amino acid sequence deduced from it, of the α-ald gene of *A. aerogenes*.

FIG. 6 shows the nucleotide sequence, and the amino acid sequence deduced from it, of the α-ald gene of *E. aerogenes*.

FIG. 17 shows the quality of the finished beers produced with the control strain VTT-A-63015 and the recombinant plasmid strains.

FIG. 19 shows the quality of the finished beers produced with the control strain VTT-A-63015 and the recombinant integrant strains.

DESCRIPTION OF THE PREFERRED EMBODIMENTS

Figure 1:
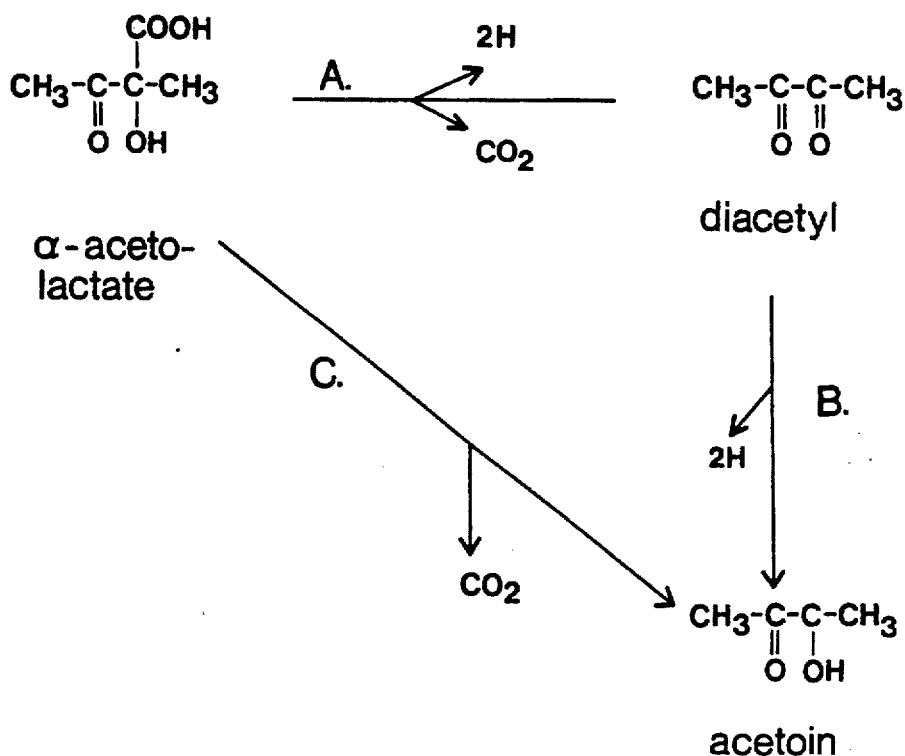
FIG. 1 shows the formation of diacetyl and acetoin from α-acetolactate.

In the following are described, as an example of an advantageous way of performing the present invention in practice, in detail the isolation of the α-ald gene from a bacterium *Aerobacter aerogenes*, according to the present taxonomy *Klebsiella terrigena* (Krieg and Holt, 1984), and from a bacterium *Enterobacter aerogenes* used in production of lambic beer, the characterization of the genes and the construction of yeast expression vectors containing the α-ald genes and the transfer of the genes to a larger brewer's yeast strain *Saccharomyces cerevisiae* using these yeast expression vectors both as autonomously replicating plasmids and as integrated to the yeast genome. It must be noted that the gene can be isolated also from other bacteria having this gene, using the same method and that the gene can also be transferred to another *Saccharomyces cerevisiae* yeast strain in accordance with the present invention.

The Bacterial and Yeast Strains and Cloning Vectors

The α-ald genes were isolated from the bacteria *Aerobacter aerogenes* VTT-E-74023 and *Enterobacter aerogenes* VTT-E-87292 (Suihko, 1989).

The cosmid bank of *A. aerogenes* was constructed using the cosmid vector p3030 (Penttilä et al., 1984). The host of the cosmid vector was *Escherichia coli* HB101 (So et al., 1978).

Subcloning and dideoxysequencing was performed using the plasmid Bluescribe M13+ (Vector cloning systems, California, U.S.A.) and the plasmid pUC19 (Boehringer Mannheim, FRG). E. coli JM109 (Yanish-Perron et al., 1985) and E. coli DH5α (Bethesda Research Laboratories, FRG) were used as hosts.

The lager brewer's yeast strain *Saccharomyces cerevisiae* VTT-A-63015 (Suihko, 1989) and the selection plasmid pET13:1 (Henderson et al., 1985) were used in yeast transformations.

The integration and expression cassettes were constructed using the plasmid pAAH5 (Ammerer, 1983) and pMA91 (Mellor et al., 1983).

Enzymes

Restriction endonucleases were provided by Boehringer Mannheim, FRG. The enzyme digestions were performed according to the manufacturers' instructions. T4-ligase was provided by Boehringer Mannheim, FRG. Calf intestinal phosphatase (CIP) and *E. coli*-DNA-polymerase I Klenow subunit were provided by Boehringer Mannheim, FRG. The lysozyme enzyme was provided by Sigma, St. Louis, U.S.A. Zymolyase 60 000 enzyme was provided by Seigaku Kogyo, Tokyo, Japan. The exonuclease III and S1 enzymes were provided by Boehringer Mannheim, FRG and Bethesda Research Laboratories, U.S.A.

Growth Media and Substrates

*E. coli* bacteria were cultivated in LB medium. Transformants were selected on L-plates containing ampicillin 100 μg/ml as the selection factor. The clones having the α-ald gene were selected on Voges-Proskauer (later VP) plates.

The commercial VP medium MAST ID33 used in the VP test was provided by the Mast Laboratories Ltd., Merseyside, UK. For α-ALDC activity measurements the bacterial clones were cultivated in the same VP medium without agar.

Acetolactic acid ethyl ester acetate used as substrate in enzyme activity measurements was provided by Oxford Organic Chemicals Ltd, Brackly Northamptonshire, UK.

For yeast transformation the yeast cells were cultivated in YPD medium. For selection of transformants NEPRA medium supplemented with 0.4 or 0.6 mM $CuSO_4$ was used as bottom agar. Transformants were maintained on NEP medium (NEPRA without sorbitol) or on wort-sugar agar. For α-ALDC activity measurement transformants were cultivated in YPD medium. For brewing trials the yeast cells were cultivated in wort-sugar solution, supplemented with 0.6 mM $CuSO_4$ for plasmid strains.

LB medium: 1% Difco Bacto tryptone, 0.5% Difco yeast extract and 1% NaCl in distilled deionized water. L-plates contain LB medium with 2% agar.

YPD solution: 1% Difco yeast extract, 2% Difco Bacto peptone, 2% glucose in deionized water.

NEPRA medium: 0.2% $MgSO_4.7H_2O$, 0.2% $(NH_4)_2SO_4$, 0.3% $KH_2PO_4$, 0.025% $CaCl_2.2H_2O$, 0.2% Difco yeast extract, 0.3% Difco Bacto peptone, 4% glucose, 1.2M sorbitol and 3% agar (Oxoid Purified Agar). After autoclaving (121° C./15 min) sterilized $CuSO_4$-solution was added to the cooled medium (50° C.) (Henderson et al., 1985).

Wort-sugar solution: Pretreated wort (11%. w/w) and 10% sucrose solution were mixed 1:1 and supplemented with 0.1% Difco yeast extract. For solid medium the solution was supplemented with 2% agar.

Methods

The methods of molecular biology, unless otherwise specified, were as described in Maniatis et al., 1982.

The VP plates were tested as follows: 1.8 g of agarose (Indubiose A37) and 60 ml of warm water was heated until the agarose was melted, cooled to 60° C. and 12 ml of freshly prepared 5% α-naphtol in 2.5N NaOH was added. This mixture was pipetted onto plates, so that colonies were covered, and formation of red colour was followed for one hour.

The VP test for *E. coli* was performed by pipetting 1 ml of broth culture, 0.3 ml of freshly prepared 5% α-naphtol in abs. ethanol and 0.1 ml of 40% KOH. The mixture was stirred vigorously and the formation of red colour was followed for half an hour.

The α-ALDC activity testing of VP positive clones was done according to the EP patent application 0128714 except that the buffer used was 0.1M phosphate pH 7.0. The acetoin formed was detected using VP test or gas chromatography (Pajunen et al., 1987).

Transformation of brewer's yeast was carried out by the protoplast method (Henderson et al., 1985, Penttilä et al., 1987). Yeast was grown to the exponential growth phase in YPD (100 ml), washed once with water and once with 1.2M sorbitol, and resuspended into 8 ml of STC-buffer (1.2M sorbitol-10 mM Tris HCl-10 mM $CaCl_2$, pH 7.6). Zymolyase (150 μg) was added and the mixture was incubated 20-40 min at 30° C. Formation of protoplasts was followed by measuring the absorbance ($Klett_{66}$) of 100 μl of cells diluted either into 5 ml of 1.2M sorbitol or into 5 ml of deionized water. When the absorbance of the cells diluted into water was 20-40% of those diluted into sorbitol, the protoplasts were washed 3 times with 1.2M sorbitol and once with STC buffer. To 200 μl of this protoplast suspension 3-4 μg of DNA was added, the maximum volume being 20 μl. The mixture was incubated 10 min at room temperature, 2 ml of TpD buffer (20% PEG 6000-10 mM Tris HCl-10 mM $CaCl_2$, pH 7.6) was added and incubation continued 30 min at room temperature. The protoplasts were centrifuged in a bench centrifuge (3000 rpm, 5 min) and resuspended with 200 μl of TpD buffer. 5 μl of protoplasts were plated in 5 ml of top agar (NEPRA medium without $CuSO_4$) onto NEPRA plates (20 ml) containing 0.4 mM or 0.6 mM $CuSO_4$. Only cells transformed with the CUP1 gene could form large colonies on these plates in about a week.

The α-ALDC activity of the yeast transformants was measured from cells grown in 5 ml of YPD medium for 17-20 h at 30° C. without shaking. The cells were centrifuged at room temperature 3000 rpm 10 min, washed with 5 ml of deionized water and resuspended into 1 ml of 0.1M phosphate buffer pH 7.0. 10 μl of Zymolyase (5 mg/ml) was added, the mixture was incubated 60 min at 37° C., and shaked vigorously to break the protoplasts. Cell debris was removed by centrifugation at room temperature 5000 rpm 10 min. 80 μl of freshly prepared hydrolysate of the diester of α-acetolactate was added and incubation continued 30-60 min at 30° C. Thereafter a VP test was carried out: 500 μl of 0.3% creatine, 600 μl of freshly prepared 5% α-naphtol in abs. ethanol and 300 μl of 40% KOH was added. The formation of red colour was followed for 20-30 min. The absorbance was measured at λ540 nm with Multiskan spectrophotometer.

The isolation of total DNA of yeast was carried out as follows: Yeast was grown in 5 ml of YPD to stationary phase (16-20 h) at 30° C. with shaking. Cells were centrifuged 5 min 5000 rpm in a bench centrifuge and resuspended with 380 μl of sorbitol solution (1.2M sorbitol-0.1M EDTA, pH 7.5). 7 μl of Zymolyase (5 mg/ml) was added and the mixture was incubated at 30° C. for 30 min. Cells were centrifuged 5 min 3500 rpm and resuspended with 690 μl of SDS solution (50 mM Tris, pH 7.5-1 mM EDTA-0.1% SDS), mixed vigorously and centrifuged in an Eppendorf centrifuge 2 min. To the supernatant 4 μl of RNAse A (5 mg/ml, Sigma) was added and incubation was carried out at 37° C. for 30 min. The mixture was extracted once with phenol and once with chloroform-isoamylalcohol (24:1). DNA was ethanol precipitated and resuspended with 50 μl of TE (50 mM Tris, pH 7.5-1 mM EDTA).

Dot blot hybridization was carried out as follows: 10 μl of total yeast DNA (or less if hybridization to the plasmid vector was studied), prepared as described above, was boiled for 10 min in 0.3M NaOH and placed on ice. The solution was made 0.1M for Tris-HCl (pH 7.5) and 1M for NH₄Ac and sucked with a "dot blot" apparatus onto nitrocellulose filter (Schleicher & Schüll, BA 85) moistened with 1M NH₄Ac. The filter was hybridized and autoradiographed according to conventional methods.

The general methods used in analysis of pilot brewings have been described in

Analytica-EBC (1987). Determination of VDK compounds and flavour compounds of the beer were carried out as described by Pajunen et al. (1987).

EXAMPLE 1.

Isolation and characterization of the gene coding for α-ALDC from *Aerobacter aerogenes*

The chromosomal DNA of *Aerobacter aerogenes* VTT-E-74023 was isolated by the phenol extraction method (Amundsen and Neville, 1979).

For the preparation of a cosmid bank the DNA was partially digested with Sau3A to obtain fragments of 30–40 kb which were then ligated to the vector p3030 digested with BamHI. The hybrid molecules were packaged in vitro into λ particles (Hohn and Murray, 1977), transferred into E. coli HB 101, and the transformants were selected on L-plates containing ampicillin.

Figure 2:
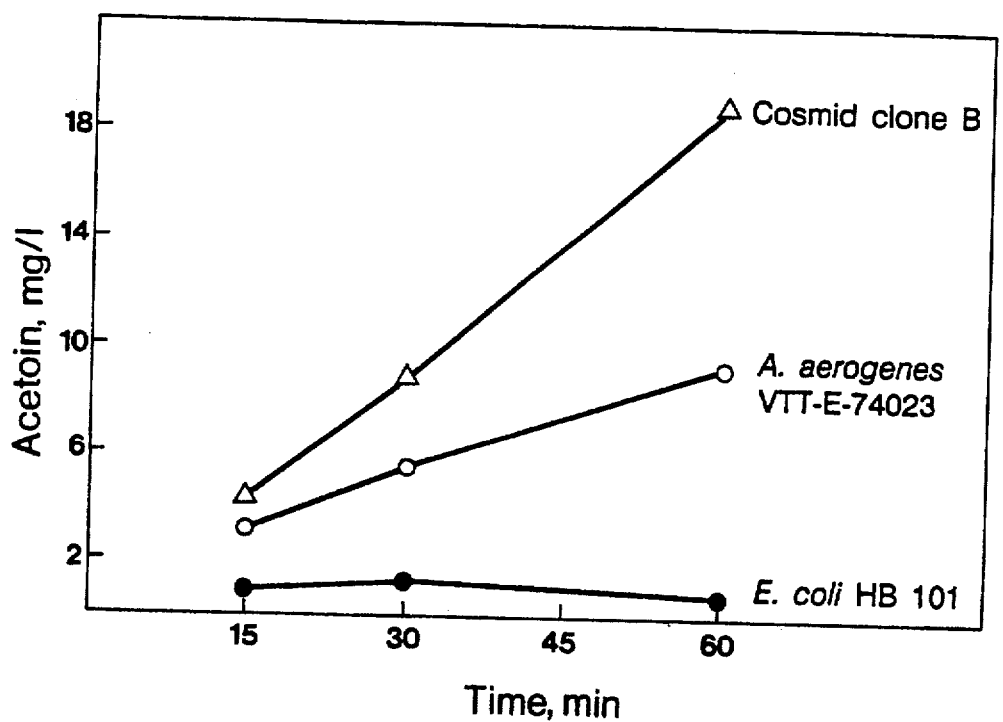
FIG. 2 shows the α-ALDC activity of *A. aerogenes* VTT-E-74023 and the cosmid clone β.

The gene bank obtained was screened for the clones containing the α-ald gene by replicaplating the colonies onto VP plates which were tested as described earlier. Clones giving a positive reaction were recovered from the original gene bank plates. The activity of one of the clones (β) was verified by measuring enzyme activity of the cell extract using α-acetolactate as substrate (FIG. 2). Direct formation of acetoin from the added α-acetolactate was detected by gas chromatography. No formation of diacetyl was observed.

Cosmid DNA was isolated from the β-clone expressing α-ALDC activity and it was partially digested with Sau3A. Fragments of 2-5 kb were ligated to the vector Bluescribe M13+ which had been cut with BamHI and phosphatase treated.

A VP positive clone carrying the plasmid pB5 with a shortened insert was isolated in the same way as the original positive clone. Deletion series were made from the *A. aerogenes* DNA of the plasmid pB5 from both strands (Henikoff, 1984). To obtain this, the plasmid pB5 was cut with SstI and Asp718 or with SphI and BamHI. The nucleotide sequence of these deletion clones was determined by the dideoxy method (Sanger et al., 1977) using plasmid sequencing (Zagursky et al., 1986). The deletion clones were tested by VP test. Also the clone containing the plasmid pMNB58 which carried a short insert was VP positive. The nucleotide sequence of the *A. aerogenes* DNA of this clone is shown in FIG. 3.

Figure 4A:
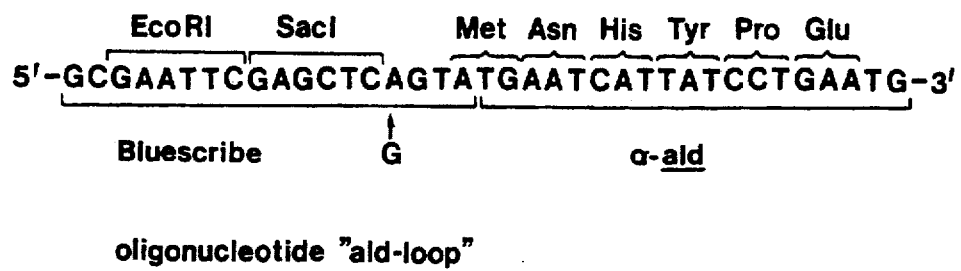
FIG. 4 shows deletion mutagenesis and mutagenesis of the start codon of the α-ald gene of *A. aerogenes*.
Figure 4B:
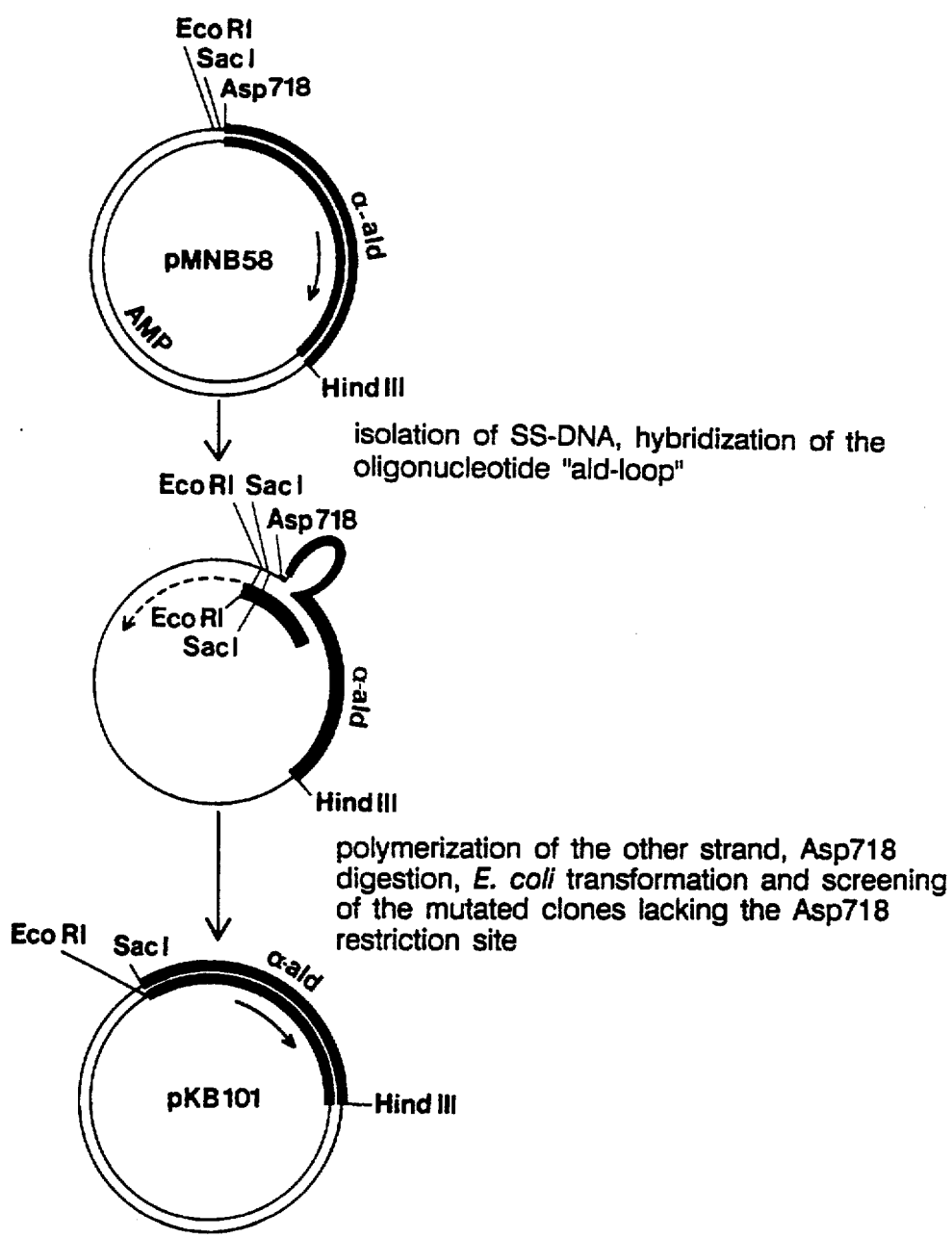

The *A. aerogenes* DNA present in the plasmid pMNB58 codes for a protein of 259 amino acids (FIG. 3). For expression in yeast, all non-coding 5' flanking region of this clone (nucleotides 50-235, FIG. 3) was looped out by deletion mutagenesis (Eghtedarzadeh and Henikoff, 1986) using a specific oligonucleotide "ald-loop" (FIG. 4). At the same time the start codon GTG (nucleotides 235-237, FIG. 3) was changed to ATG which is recognized by yeast, and the nucleotide G at the −3 position to A to obtain efficient expression in yeast. The amount of unmutagenized background molecules was reduced by digesting the synthetized molecules with Asp718 before transformation into *E. coli* (FIG. 4). Differently from the published method (Eghtedarzadeh and Henikoff, 1986) no S1 enzyme was used. Deleted clones were screened for by restriction enzyme digests, and the deletions were confirmed by sequencing. The plasmid pKB101 (FIG. 4) carried the correct deletion.

EXAMPLE 2

Isolation and characterization of the gene coding for α-ALDC from *Enterobacter aerogenes*

Chromosomal DNA was isolated from *Enterobacter aerogenes* VTT-E-87292 (Amundsen and Neville, 1979). A Southern map was established from the genomic DNA by using the gene isolated from *Aerobacter aerogenes* VTT-E-74023 as a probe. The probe was isolated from the plasmid pMNB58 (FIG. 3) as a 1.16 kb Asp718-HindIII fragment using LGT (low gelling temperature) agarose electrophoresis. The isolated fragment was labelled to specific activity of $>10^8$ cpm/μg using α-$^{32}$P-dCTP and Klenow polymerase with the random primer labeling kit (Boehringer Mannheim, FRG). The *Enterobacter aerogenes* DNA (400 ng) was digested with different restriction enzymes and run in an agarose gel and the DNAs were blotted onto Gene Screen filter (NEN Research Products, Du Pont, FRG). The conditions for heterologous hybridization when using the probe mentioned above were optimized and were 35° C., 40% formamide, 6×SSC (0.9M NaCl-90 mM natriumcitrate, pH 7.0), 10×Denhardt's (0.2% Ficoll-0.2% polyvinylpyrrolidone-0.2% bovine serum albumin), 0.5% SDS, 100 μg/ml denatured herring sperm DNA and 10 μg/ml poly(A). Prehybridization was carried out in these conditions for 3–16 h, the denatured labelled probe was added and hybridization was continued over night at 35° C. The filters were washed 3 times at 42° C. with 6×SSC. Hybridization was detected by autoradiography.

The Southern hybridization showed that a 4.5 kb AhaIII fragment as well as a 3.5 kb BamHI fragment could contain the complete α-ald gene of *E. aerogenes*. A preparative isolation of these fragments was carried out as follows: 100 μg of *E. aerogenes* VTT-E-87292 chromosomal DNA was digested with 240 U of restriction enzymes for 5 h at 37° C. in the optimal conditions for these enzymes. The samples were phenol extracted and precipitated before preparative LGT agarose gel electrophoresis (0.7% agarose). After the run slices of 1-2 mm were cut out from the unstained gel from the positions of the 4.5 kb AhaIII fragment and the 3.5 kb BamHI fragment. DNA was isolated separately from these slices and 2 μg of it was used for "dot blot hybridization" (see methods) with the above mentioned probe. The fragment carrying the α-ald gene was localized in both cases in only one of the gel slices isolated.

200 ng of the DNA fraction enriched for the 4.5 kb AhaIII fragment was ligated with 100 ng of pUC19 vector in the volume of 15 μl. The pUC19 vector had been cut with EcoRI and made blunt-ended with Klenow and dATP and dTTP. *E. coli* DH5α was transformed with 20 ng of the ligation mixture. The transformant colonies obtained were applied onto nitrocellulose filters and VP plates. In the same way, 200 ng of the DNA fraction containing the 3.5 kb BamHI fragment was ligated with 100 ng of pUC19 vector which was cut with BamHI and phosphatase treated. 20 ng of the ligation mixture was transformed into *E. coli* DH5α cells.

Figure 5A:
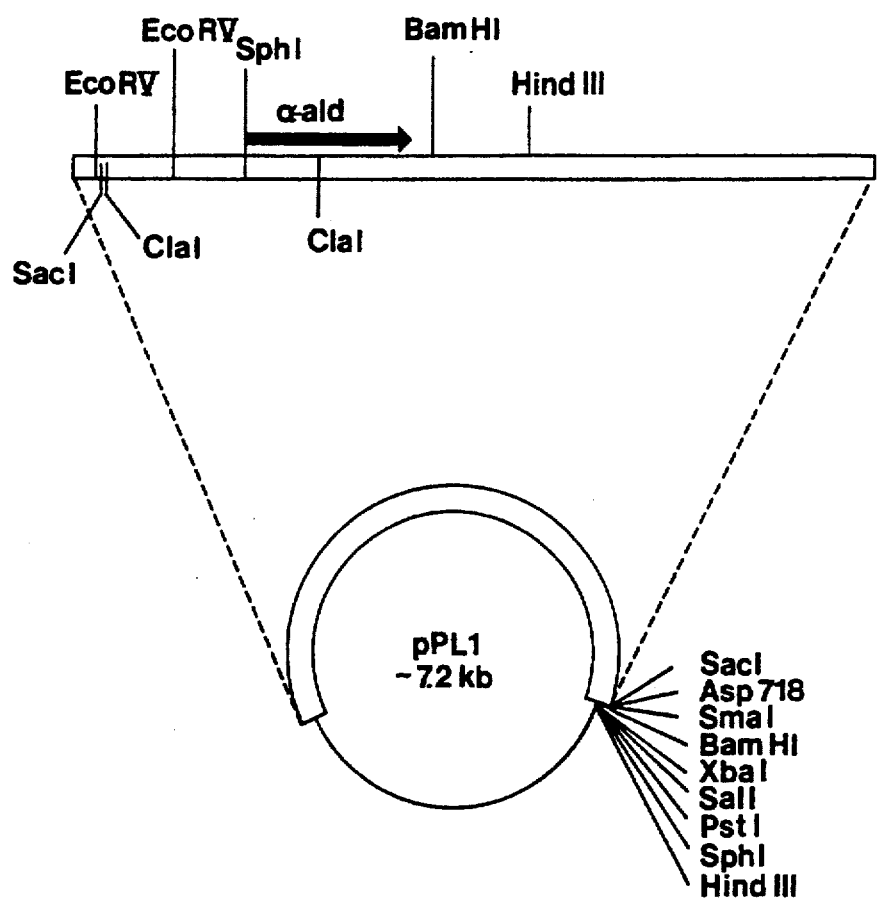
FIG. 5 shows the restriction map of the clones pPL1 and pPL2 which carry the α-ald gene of *E. aerogenes*.

About two percent of the clones transformed with the pUC19 vector, ligated to the DNA fraction containing the 4.5 kb AhaIII fragment, were VP positive, but no positive clones were found amongst the clones transformed with DNA from the fraction containing the 3.5 kb BamHI fragment. The VP positive clones hybridized with the 1.16 kb long heterologous *A. aerogenes* probe indicating that the positive clones carried the 4.5 kb AhaIII fragment. One of these clones was named pPL1 (FIG. 5A).

Figure 5B:
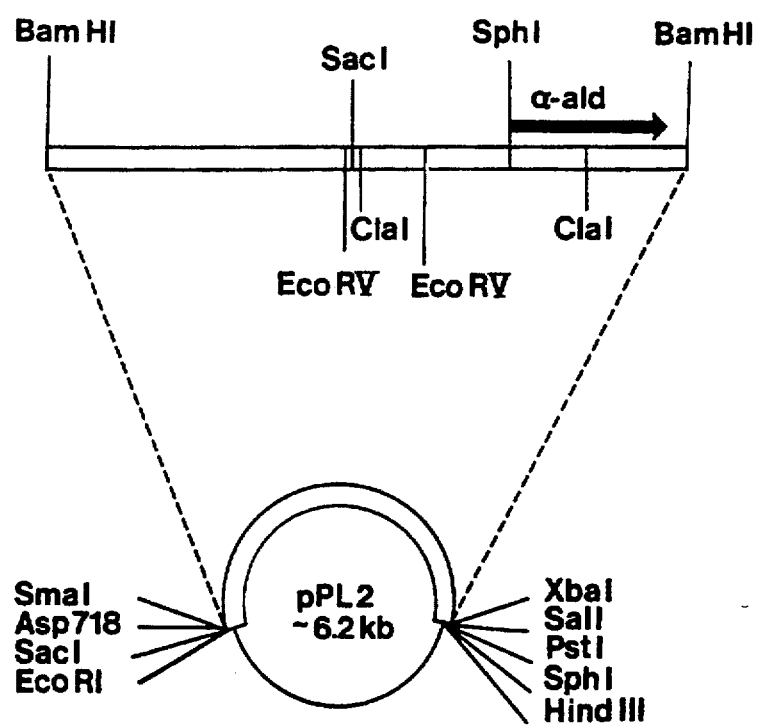

Ten percent of the clones transformed with the 3.5 kb BamHI fragment hybridized with the *A. aerogenes* probe and thus contained the α-ald gene or parts of it. One of these clones was pPL2 (FIG. 5B).

The region containing the α-ald gene of the plasmid pPL2 was sequenced starting from the BamHI site (Zagursky et al., 1986) using synthetic oligonucleotides (University of Helsinki, Department of Medical Chemistry) as primers. The nucleotide sequence obtained and the deduced aminoacid sequence is shown in FIG. 6.

A 1.4 kb long EcoRV-BamHI fragment was isolated from the plasmid pPL2 (FIG. 5B) using LGT gel electrophoresis and was made blunt-ended with S1 nuclease. The fragment was cloned to Bluescribe M13+ vector which had been cut with SphI, S1 treated and dephosphorylated. The plasmid pPL3 obtained carried the α-ald gene in the same orientation between the polylinker sequences as the plasmid pPL2.

Single-stranded DNA was prepared from the plasmid pPL3 and that was hybridized with the oligonucleotide "eld-loop" (FIG. 7) to remove the non-coding 5' flanking region of the α-ald gene by deletion mutagenesis (Eghtedarzadeh and Henikoff, 1986). After Klenow and ligase treatment the DNA was cut with PstI to enrich the mutated clones before transformation into *E. coli*. Plasmid pPL4 (FIG. 7) was obtained and the relevant part of it was sequenced to verify the correctness of the deletion. The α-ald gene could be isolated from the plasmid pPL4 as a SalI-HindIII fragment for ligation to the yeast expression vectors.

EXAMPLE 3

Construction of yeast plasmids carrying the α-ald gene of *Aerobacter aerogenes*

Figure 8:
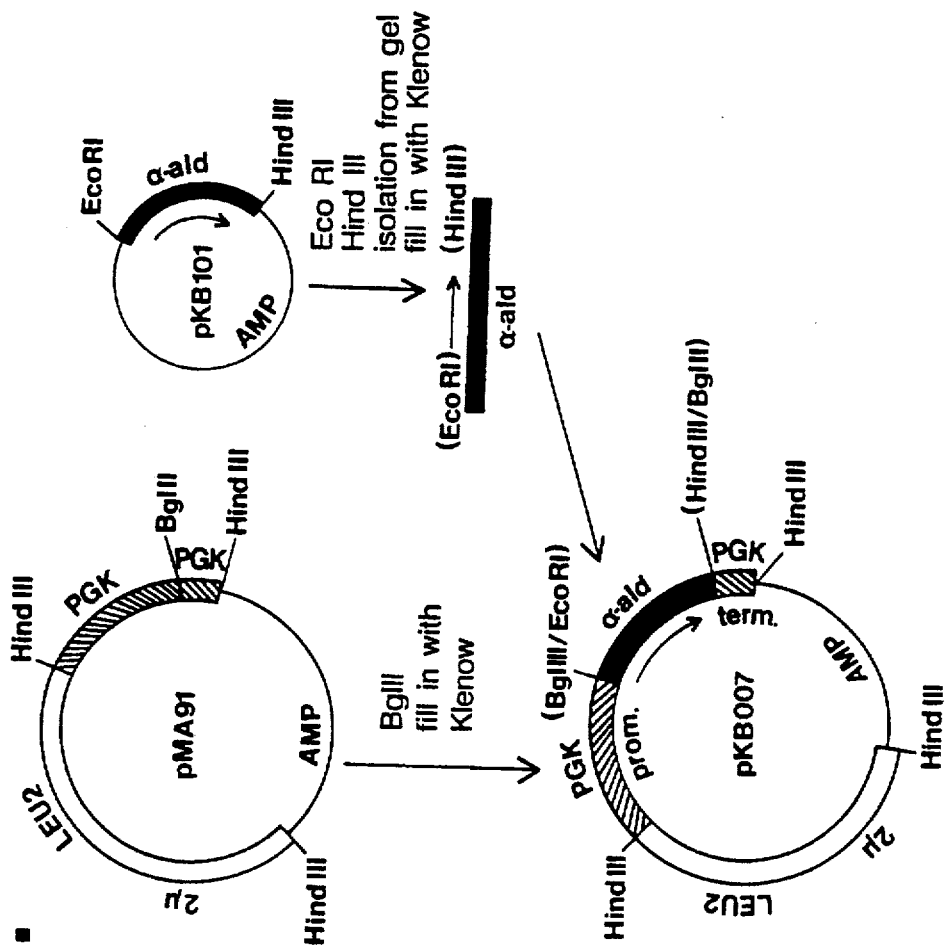
FIG. 8 shows the construction of the yeast plasmid pKB002 which carries the α-ald gene of *A. aerogenes*.
Figure 8:
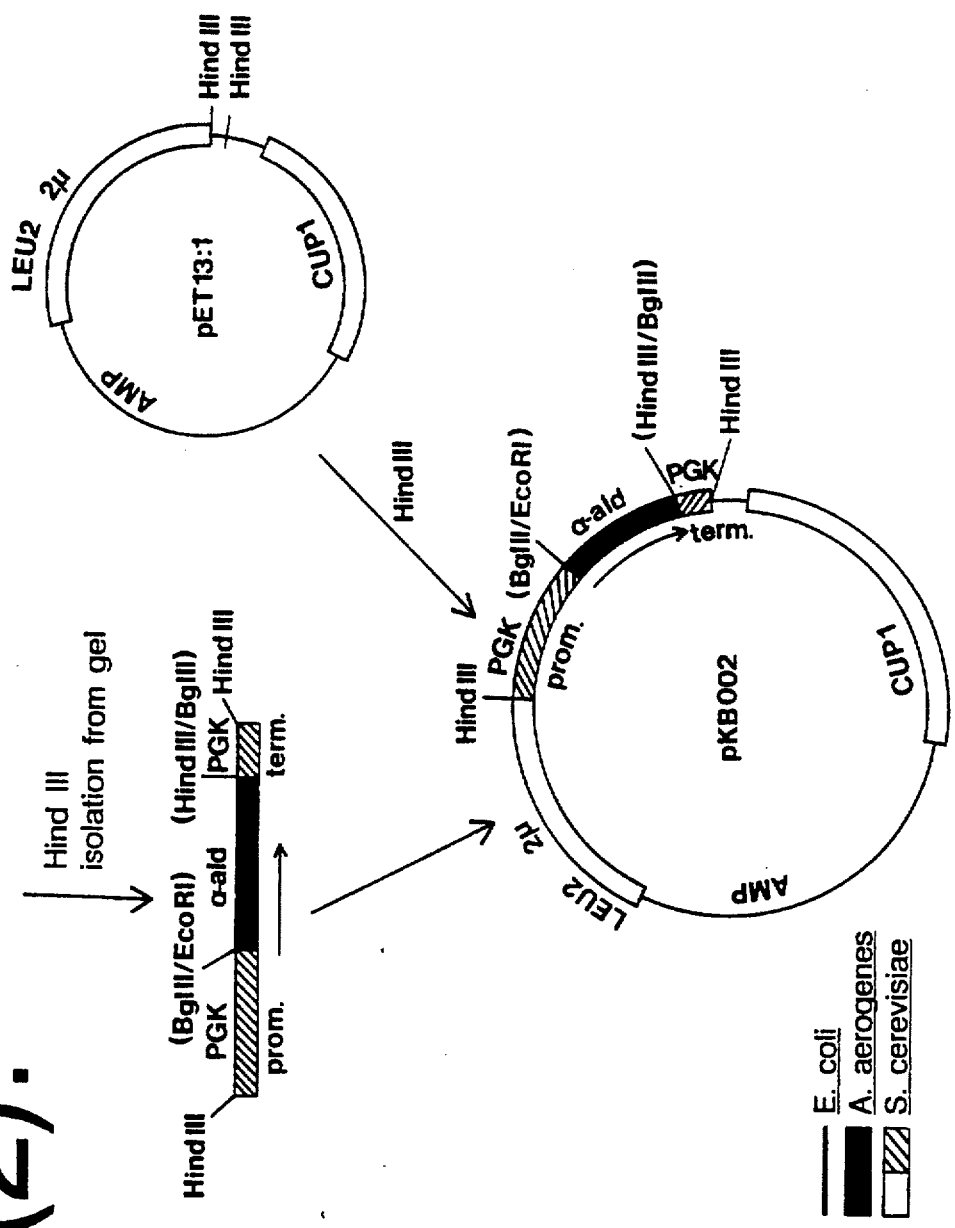

The plasmid pKB101 (FIG. 4) was digested with EcoRI and HindIII and the 0.95 kb long fragment carrying the α-ald gene was isolated from a LGT gel. The fragment was made blunt-ended with Klenow enzyme and was ligated in between the promoter and terminator regions of the yeast phosphoglycerokinase (PGK1) gene of the plasmid pMA91 which had been cut with BglII, made blunt-ended with Klenow and phosphatase treated. The plasmid pKB007 (FIG. 8) obtained carries the α-ald gene in the correct orientation towards the PGK1 promoter.

The PGK1/α-ald expression cassette was isolated from the plasmid pKB007 as a HindIII fragment of about 2.7 kb using LGT gel electrophoresis. The fragment was ligated to the plasmid pET13:1 which had been cut with HindIII and phosphatase treated. The plasmid pKB002 (FIG. 8) was obtained.

Figure 9:
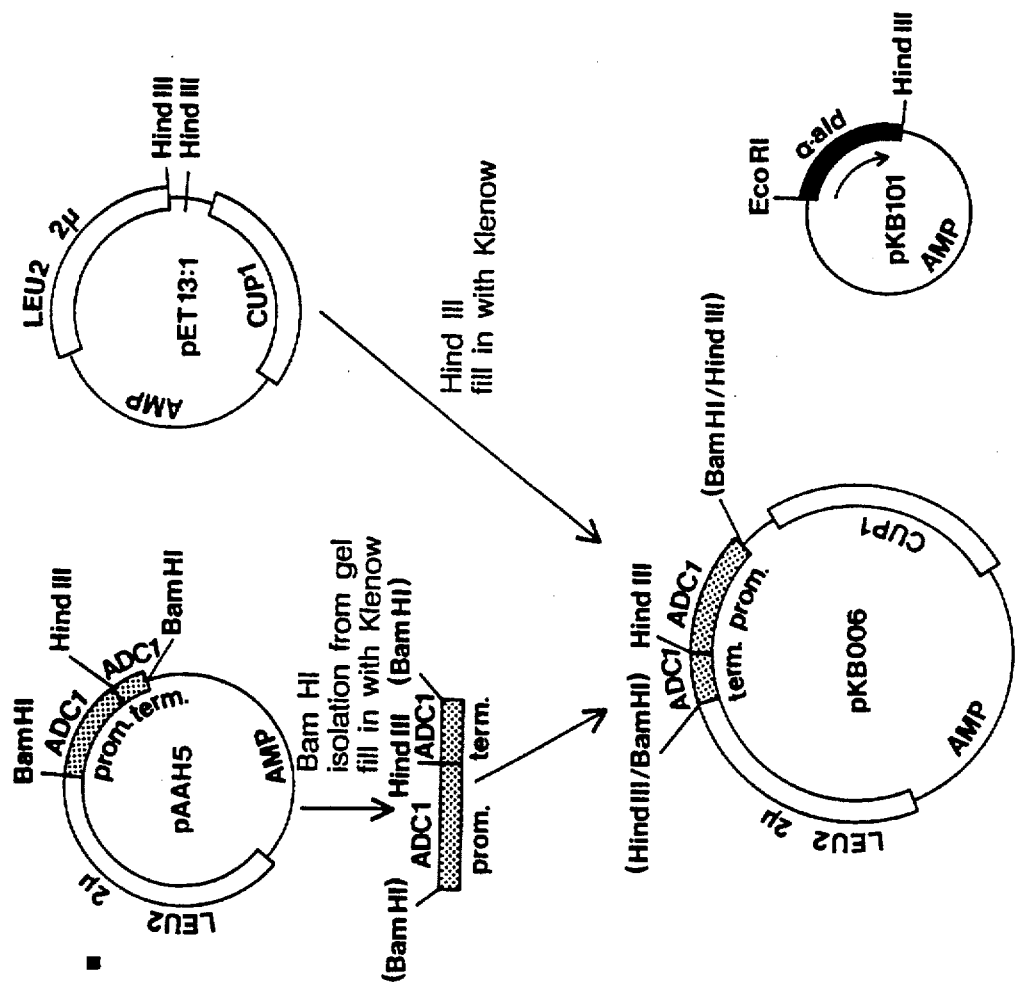
FIG. 9 shows the construction of the yeast plasmid pKB003 which carries the α-ald gene of *A. aerogenes*.
Figure 9:
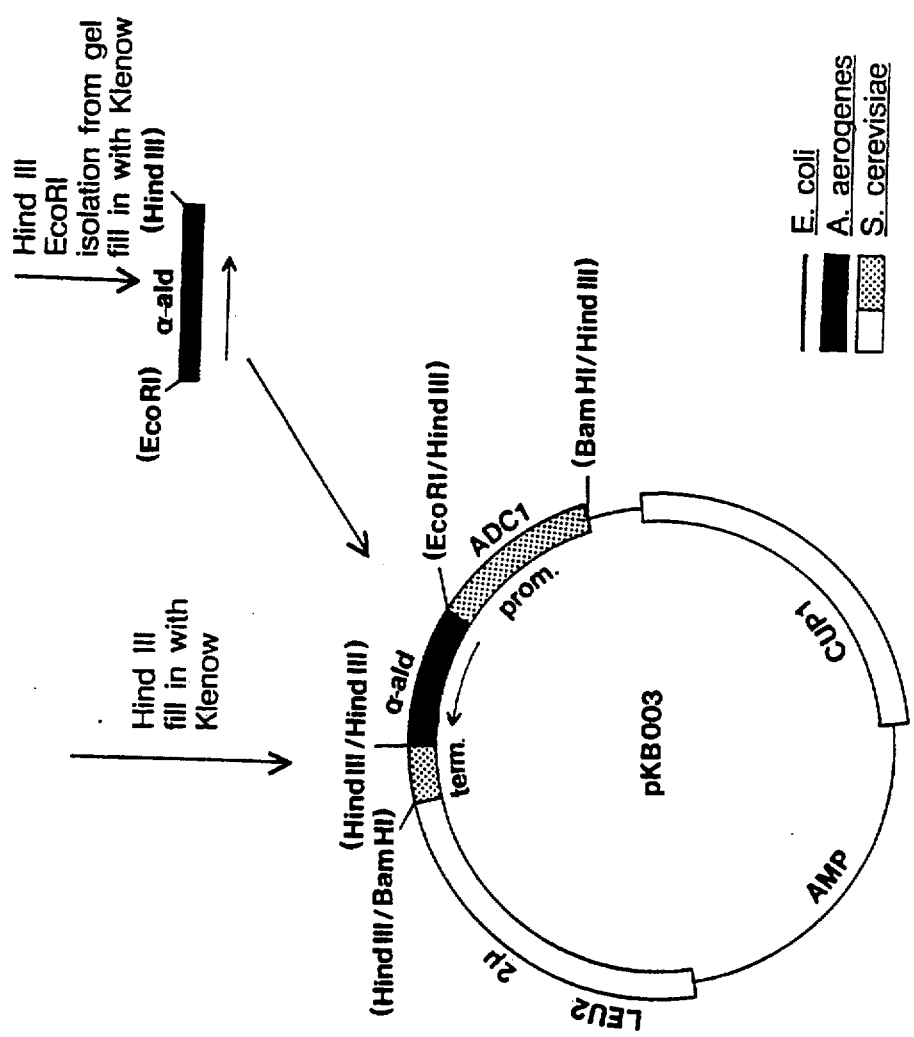

To express the α-ald gene in yeast under control of the ADC1 promoter, the plasmid pKB006 (FIG. 9) was first constructed. The plasmid pET13:1 was digested with HindIII, the ends were made blunt-ended with Klenow, phosphatase treated and the molecules were ligated with a 1.95 kb long BamHI fragment obtained from the plasmid pAAH5 and made blunt-ended with Klenow. This BamHI fragment carried the promoter and terminator regions of the yeast ADC1 gene. The plasmid pKB006 obtained was cut with HindIII, the ends were filled in with Klenow and ligated with the EcoRI-HindIII fragment of the plasmid pKB101 described above which carried the α-ald gene. The plasmid pKB003 (FIG. 9) contains the α-ald gene in the correct orientation in regard to the ADC1 promoter (FIG. 9).

EXAMPLE 4

Construction of yeast plasmids carrying the α-ald gene of *Enterobacter aerogenes*

To couple the α-ald gene of *E. aerogenes* to the PGK1 promoter, the promoter and terminator regions of the PGK1 gene were first released from the vector pMA91 as a HindIII fragment, and the fragment was cloned at the HindIII site of the vector Bluescribe M13+. Plasmid pKB104 (FIG. 10) was obtained.

Figure 10:
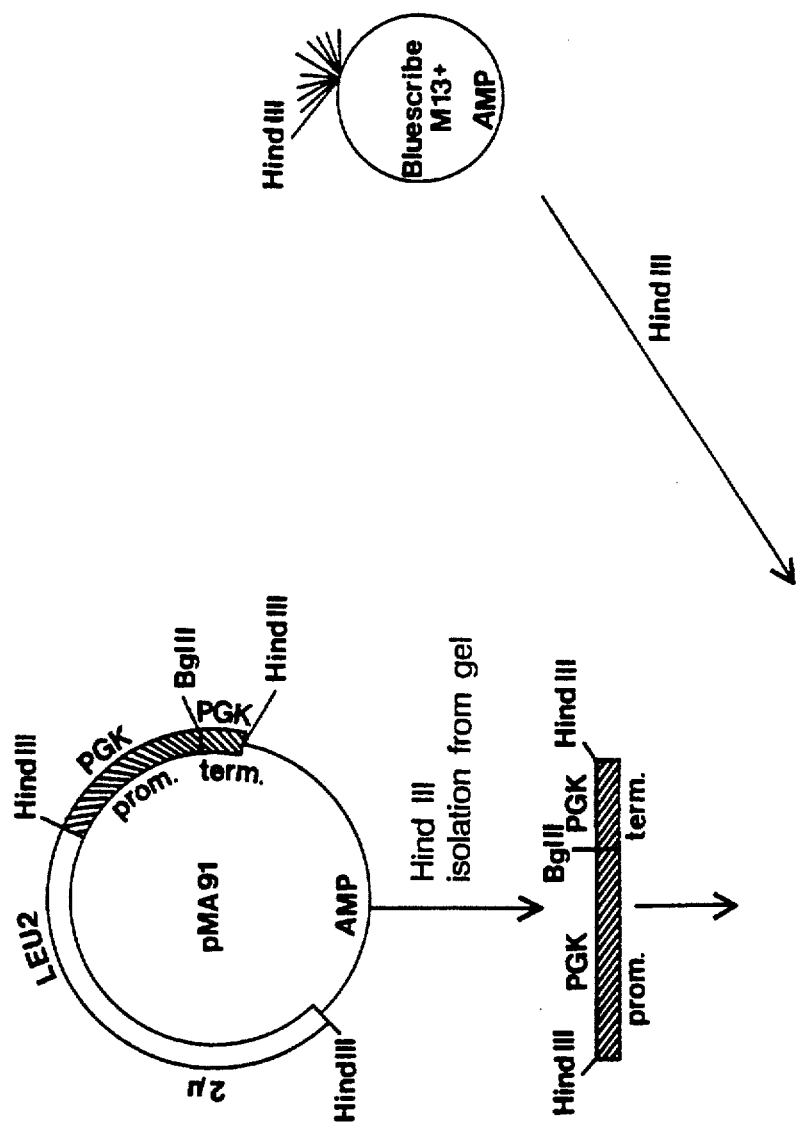
FIG. 10 shows the coupling of the α-ald gene of *E. aerogenes* to the regulatory regions of the PGK1 gene.
Figure 10:
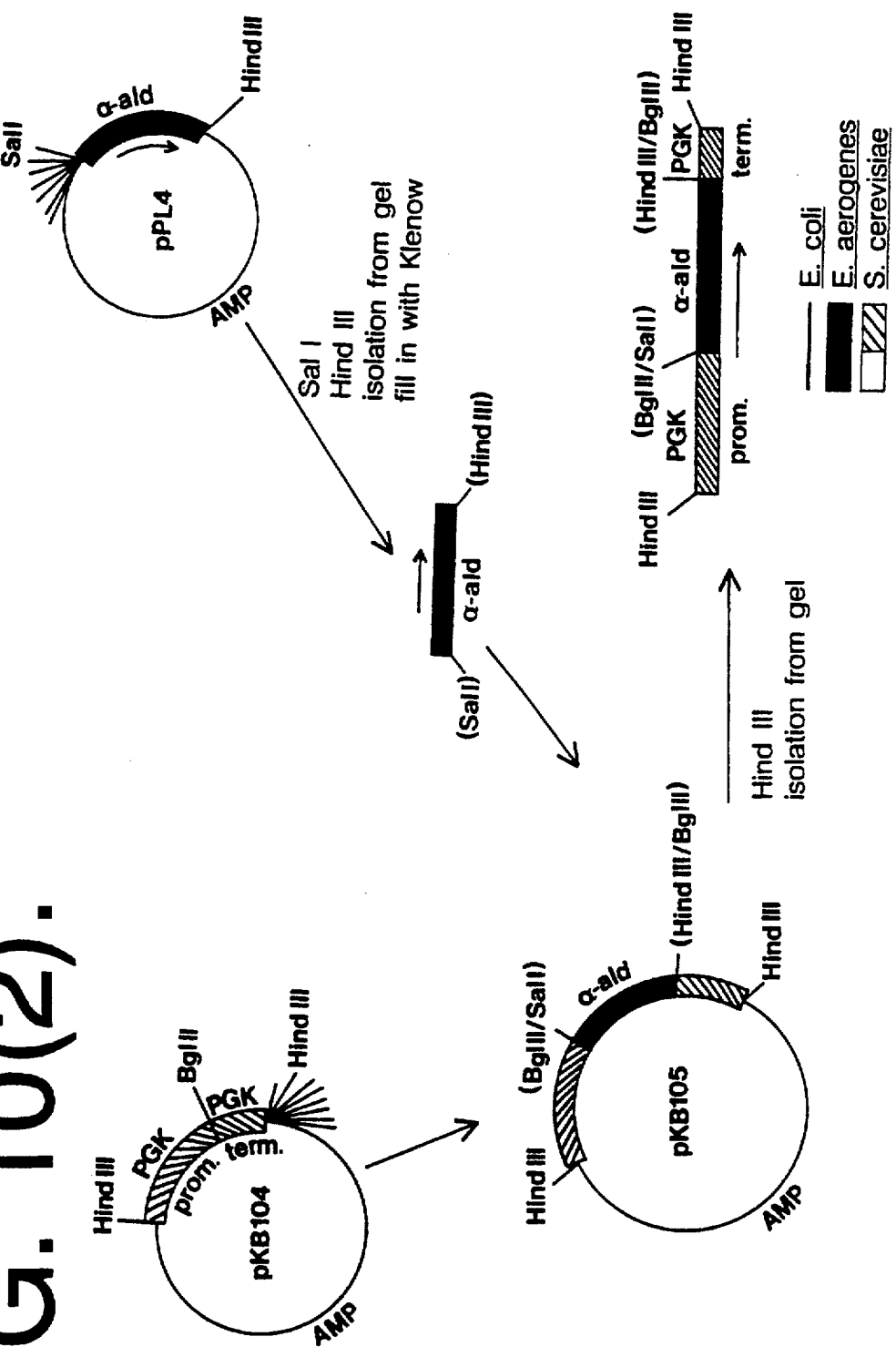

The α-ald gene of *E. aerogenes* was released from the plasmid pPL4 as a 0.9 kb long SalI-HindIII fragment, the ends were filled in with Klenow and the fragment was cloned to the plasmid pKB104 which had been cut with BglII and filled in with Klenow. The plasmid pKB105 was obtained which carried the α-ald gene in the correct orientation towards the PGK1 promoter (FIG. 10).

Figure 11:
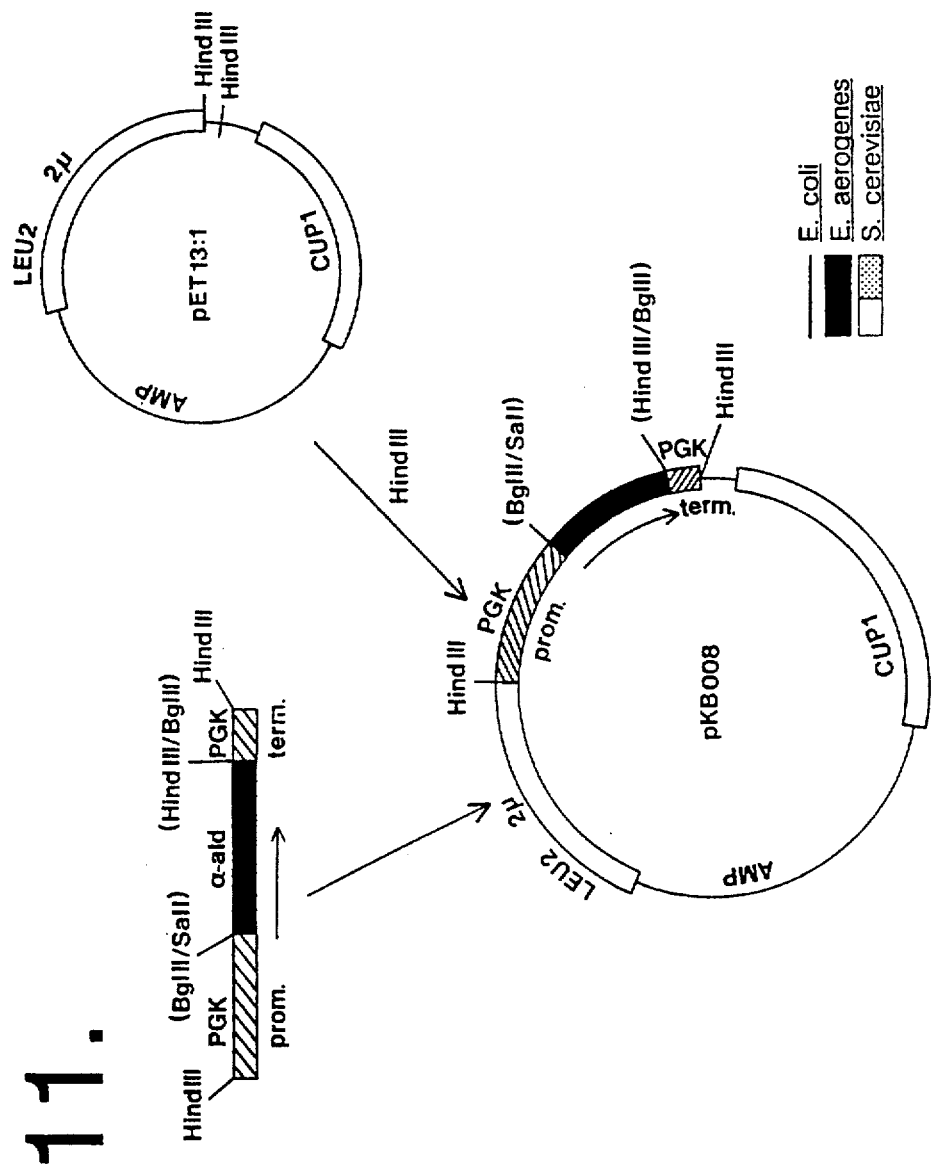
FIG. 11 shows the construction of the yeast plasmid pKB008 which carries the α-ald gene of *E. aerogenes*.

The PGK1/α-ald cassette was released from the plasmid pKB105 with HindIII and cloned at the HindIII site of the plasmid pET13:1. Plasmid pKB008 (FIG. 11) was obtained and transformed into brewer's yeast (example 7).

Figure 12:
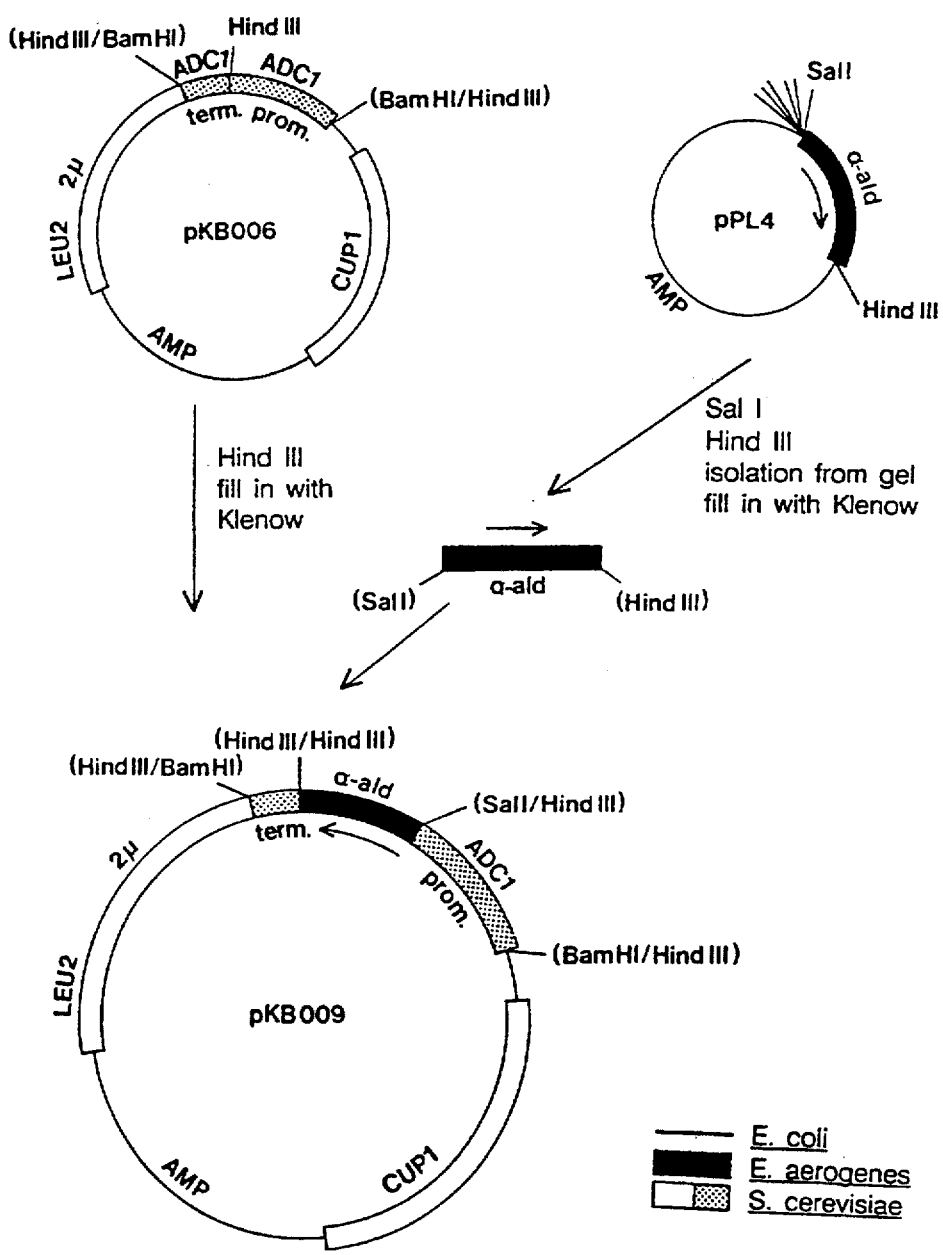
FIG. 12 shows the construction of the yeast plasmid pKB009 which carries the α-ald gene of *E. aerogenes*.

In order to transfer the α-ald gene into brewer's yeast under the control of the ADC1 promoter, the gene was first released from the plasmid pPL4 as a 0.9 kb long SalI-HindIII fragment and filled in with Klenow. This fragment was cloned to the vector pKB006 which was cut with HindIII and made blunt-ended with Klenow. The α-ald gene is in the correct orientation towards the ADC1 promoter in the plasmid pKB009 (FIG. 12).

EXAMPLE 5

Construction of DNA fragments for chromosomal integration of the α-ald gene of *Aerobacter aerogenes* into brewer's yeast The plasmid pKB007 (FIG. 8) carries the α-ald gene of *A. aerogenes* coupled in between the promoter and terminator of the yeast PGK1 gene. This PGK1/α-ald expression cassette was released from the plasmid pKB007 as a 2.7 kb long HindIII fragment which was isolated from a LGT agarose gel. The ends of the molecules were made blunt with Klenow and the fragment was transformed into brewer's yeast (example 8).

Figure 13:
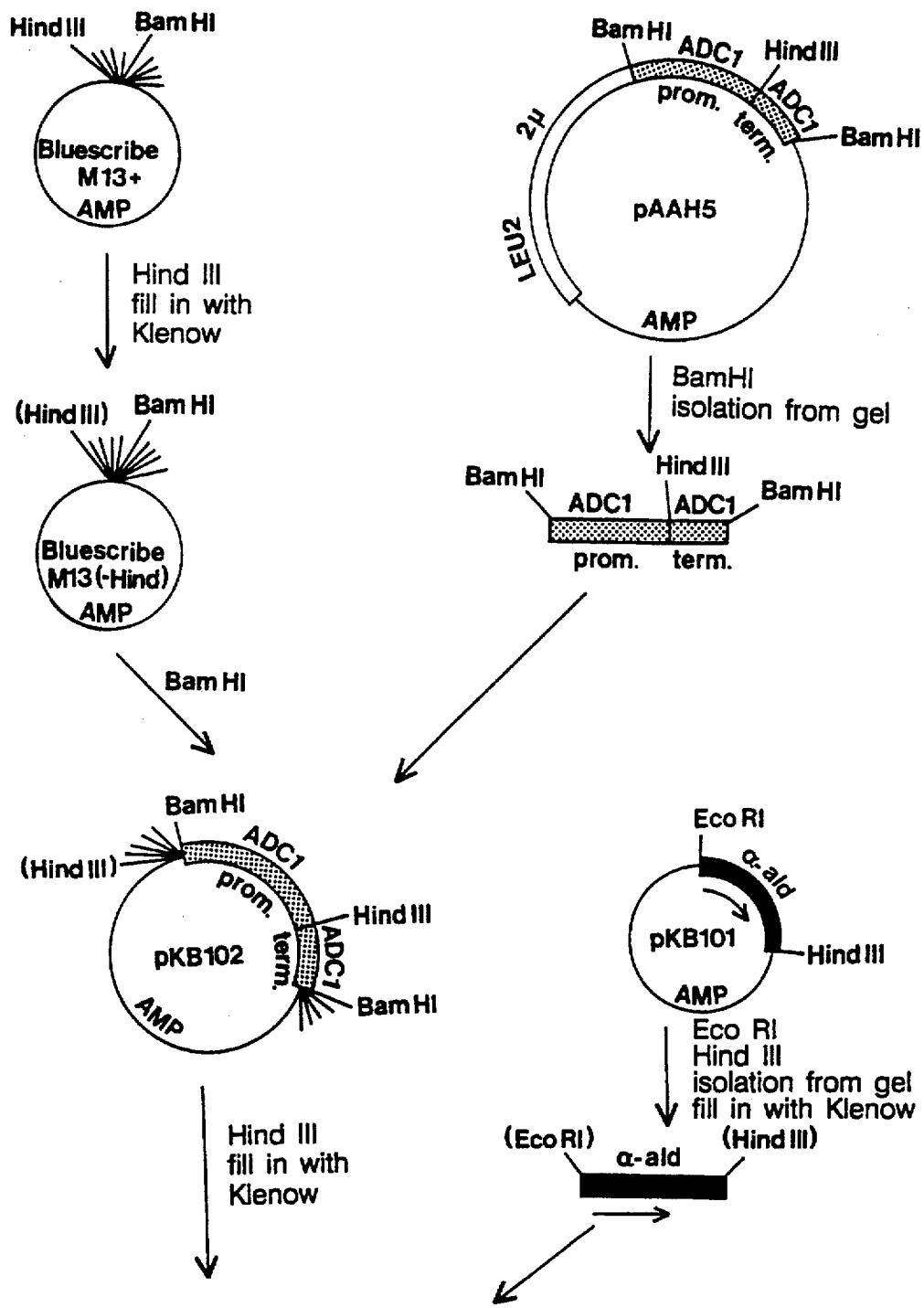
FIG. 13 shows the construction of the ADC1/α-ald-expression cassette for integration of the α-ald gene of *A. aerogenes* to the yeast chromosome.

To obtain a similar ADC1/α-ald expression cassette for yeast transformation, the cassette was first built in a Bluescribe M13+ vector (FIG. 13). The HindIII site of the Bluescribe M13+ vector was first removed by cutting the vector with HindIII, filling in the ends generated with Klenow and recirculating of the molecules. The ADC1 promoter and terminator were isolated from the vector pAAH5 as a 1.95 kb BamHI fragment, which was ligated to the BamHI site of the vector Bluescribe M13+ wherefrom the HindIII site had been removed. The plasmid obtained, pKB102, was cut with HindIII, the ends were filled in with Klenow, phosphatase treated and the molecules were ligated with a blunt-ended EcoRI-HindIII fragment of the plasmid pKB101 which carried the α-ald gene. From the resulting plasmid pKB103 (FIG. 13) the ADC1/α-ald expression cassette was released with BamHI, the ends were filled in with Klenow and the molecules transformed into brewer's yeast using co-transformation (example 8).

EXAMPLE 6

Construction of DNA molecules for the chromosomal integration of the α-ald gene of *Enterobacter aerogenes* into brewer's yeast The PGK1/α-ald expression cassette carrying the *E. aerogenes* gene was released as a 2.7 kb long HindIII fragment from the plasmid pKB105 (FIG. 10). The fragment was made blunt-ended with Klenow and co-transformed into brewer's yeast (example 8).

Figure 14:
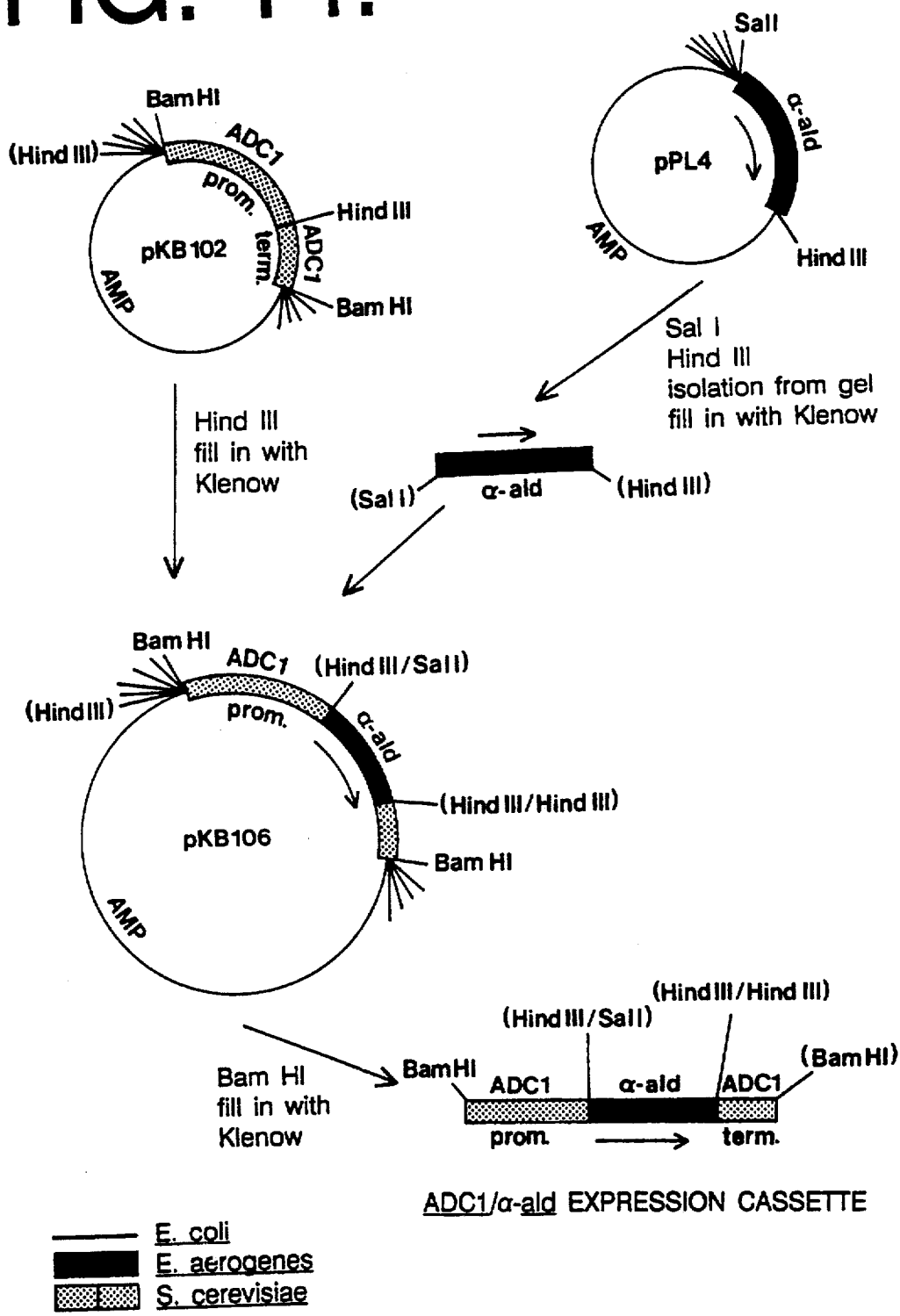
FIG. 14 shows the construction of the ADC1/α-ald-expression cassette for integration of the α-ald gene of *E. aerogenes* to the yeast chromosome.

For chromosomal integration of the gene coupled to the ADC1 promoter, the α-ald gene was first released from the plasmid pPL4 as a SalI-HindIII fragment. The fragment was filled in with Klenow and was ligated with the plasmid pKB102 which had been cut with HindIII and filled in with Klenow. In the resulting plasmid pKB106 (FIG. 14), the α-ald gene is in the correct orientation in regard to the ADC1 promoter. The ADC1/α-ald expression cassette was released from the plasmid pKB106 with BamHI, the ends were filled in with Klenow and the molecules were co-transformed into brewer's yeast (example 8).

EXAMPLE 7

Construction of brewer's yeast strains producing α-ALDC: transformation with plasmids The plasmid pKB002 which carries the α-ald gene of *A. aerogenes* coupled to the yeast PGK1 promoter (FIG. 8), and the plasmid pKB003 in which the gene is coupled to the yeast ADC1 promoter (FIG. 9), and the corresponding plasmids pKB008 (FIG. 11) and pKB009 (FIG. 12) which carry the α-ald gene of *E. aerogenes*, were transferred into the brewer's yeast strain VTT-A-63015 using protoplast transformation (see methods).

The transformants were selected on NEPRA plates containing copper (0.4 mM or 0.6 mM CuSO$_4$ in the bottom agar) on the basis of the function of the yeast CUP1 gene present in the plasmids. The transformants obtained were grown on NEP plates (NEPRA without sorbitol) containing 0.6 mM CuSO$_4$. The expression of the α-ald in yeast was detected by measuring the α-ALDC activity of the cell extracts of the transformants as described before.

The brewer's yeast strains VTT-A-87083 and VTT-A-87076, transformed with plasmids pKB002 (regulatory regions of the PGK1 gene) and pKB003 (regulatory regions of the ADC1 gene), respectively, carrying the α-ald gene of *A. aerogenes* showed α-ALDC activity, as well as the corresponding strains VTT-A-88087 and VTT-A-88088 transformed with plasmids pKB008 and pKB009, respectively, carrying the α-ald gene of *E. aerogenes*. The strains have been deposited in VTT Collection of Industrial Microorganisms (Suihko, 1989).

EXAMPLE 8

Construction of brewer's yeast strains producing α-ALDC: chromosomal integration of the α-ald genes In order to obtain brewer's yeast strains containing minimal amounts of foreign DNA and otherwise similar to the original strain, only the α-ald genes coupled to the regulatory regions of the yeast PGK1 or the ADC1 gene was transferred to yeast. Using the method described below, the endogenous ADC1 or the PGK1 locus of yeast is replaced with the α-ald genes by homologous recombination.

Figure 7A:
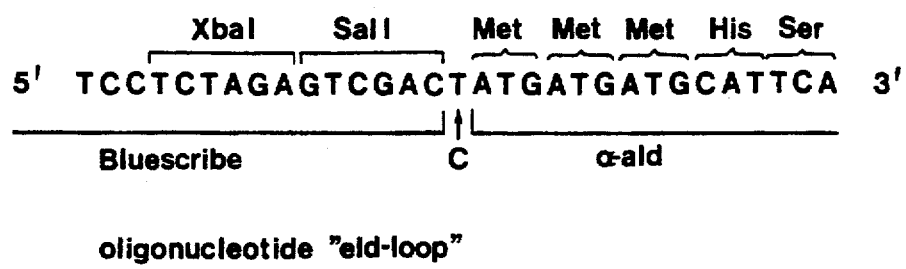
FIG. 7 shows deletion mutagenesis of the α-ald gene of *E. aerogenes*.
Figure 7B:
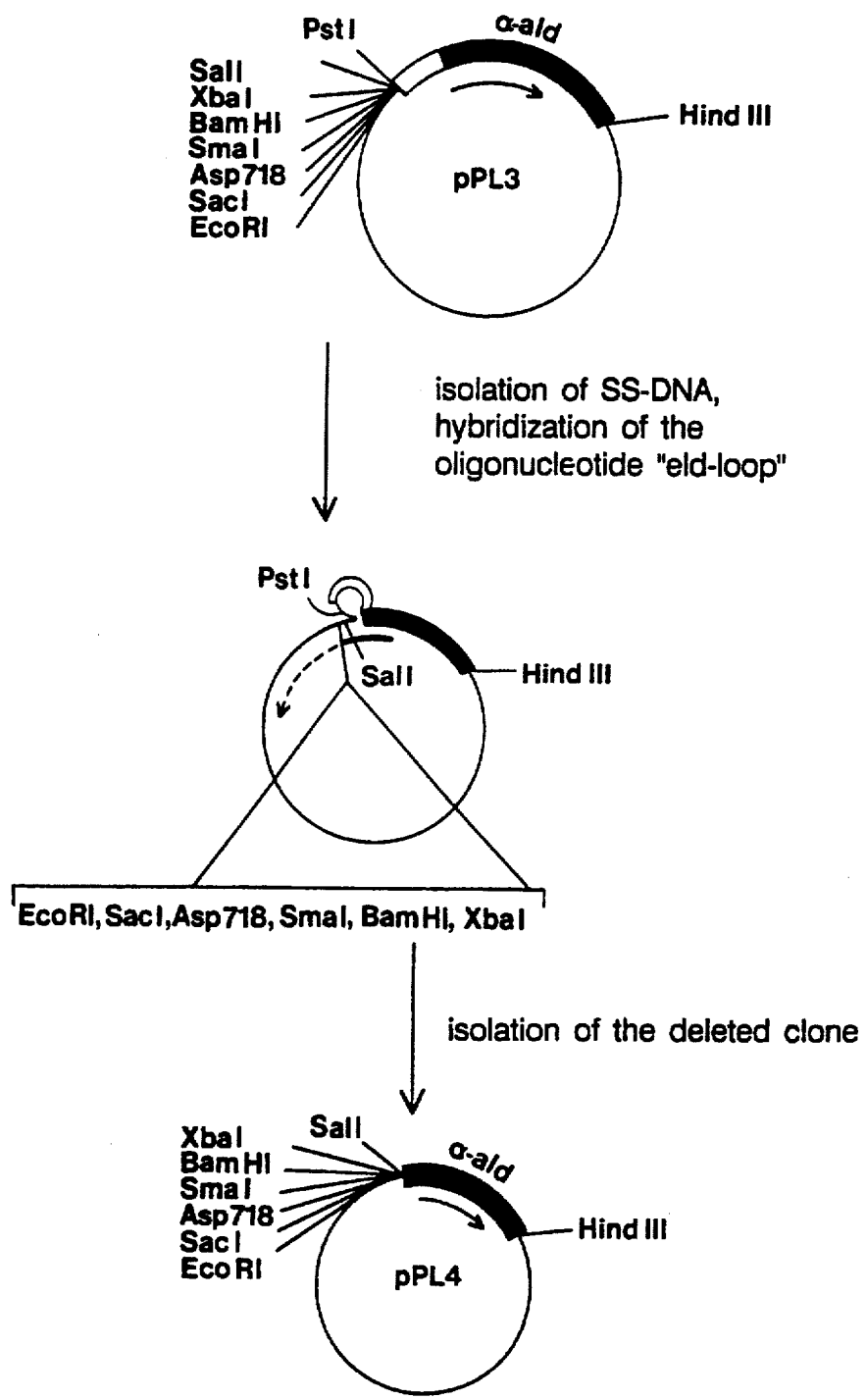
Figure 15:
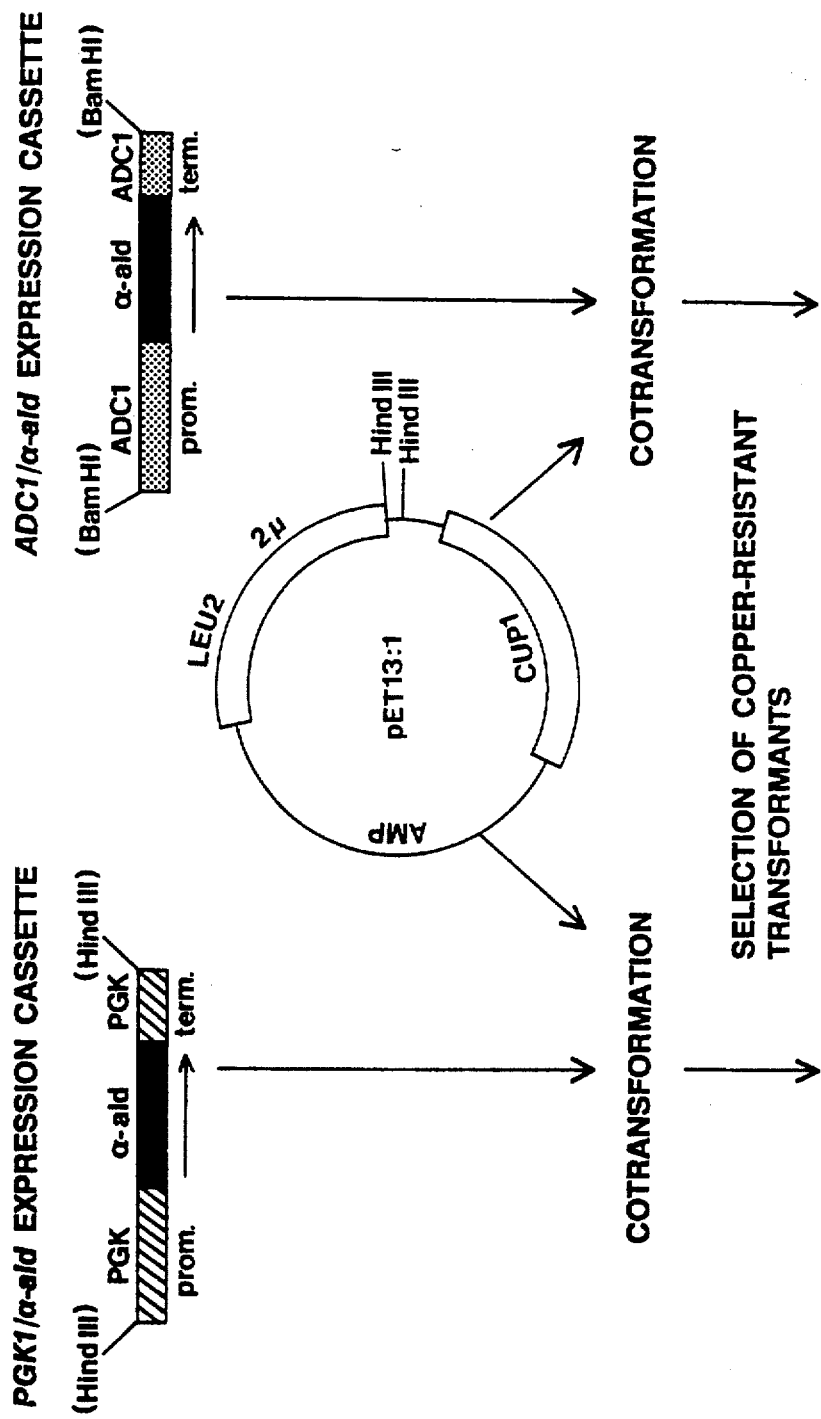
FIG. 15 shows the integration of the PGK1/α-ald- and ADC1/α-ald-expression cassettes, which carry the α-ald gene to the yeast chromosome by co-transformation.
Figure 15:
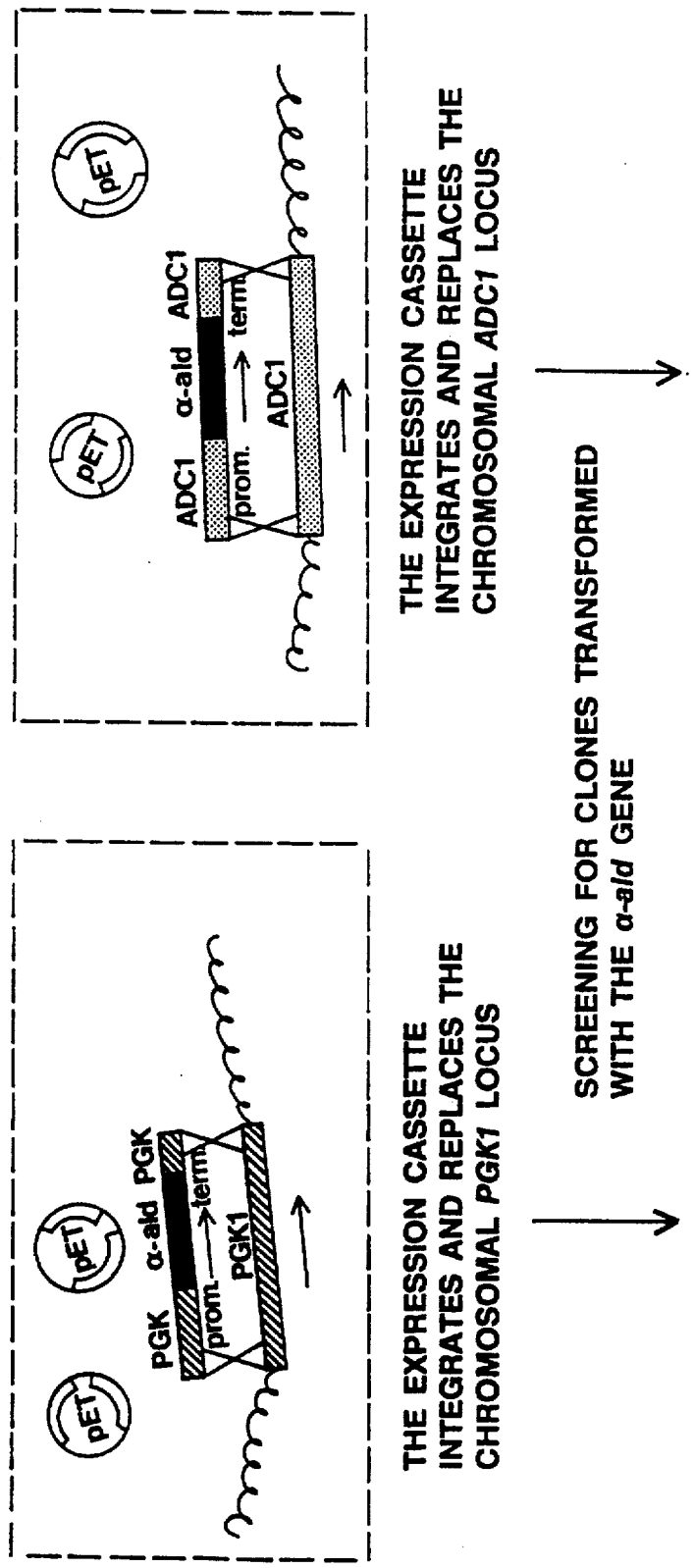
Figure 15:
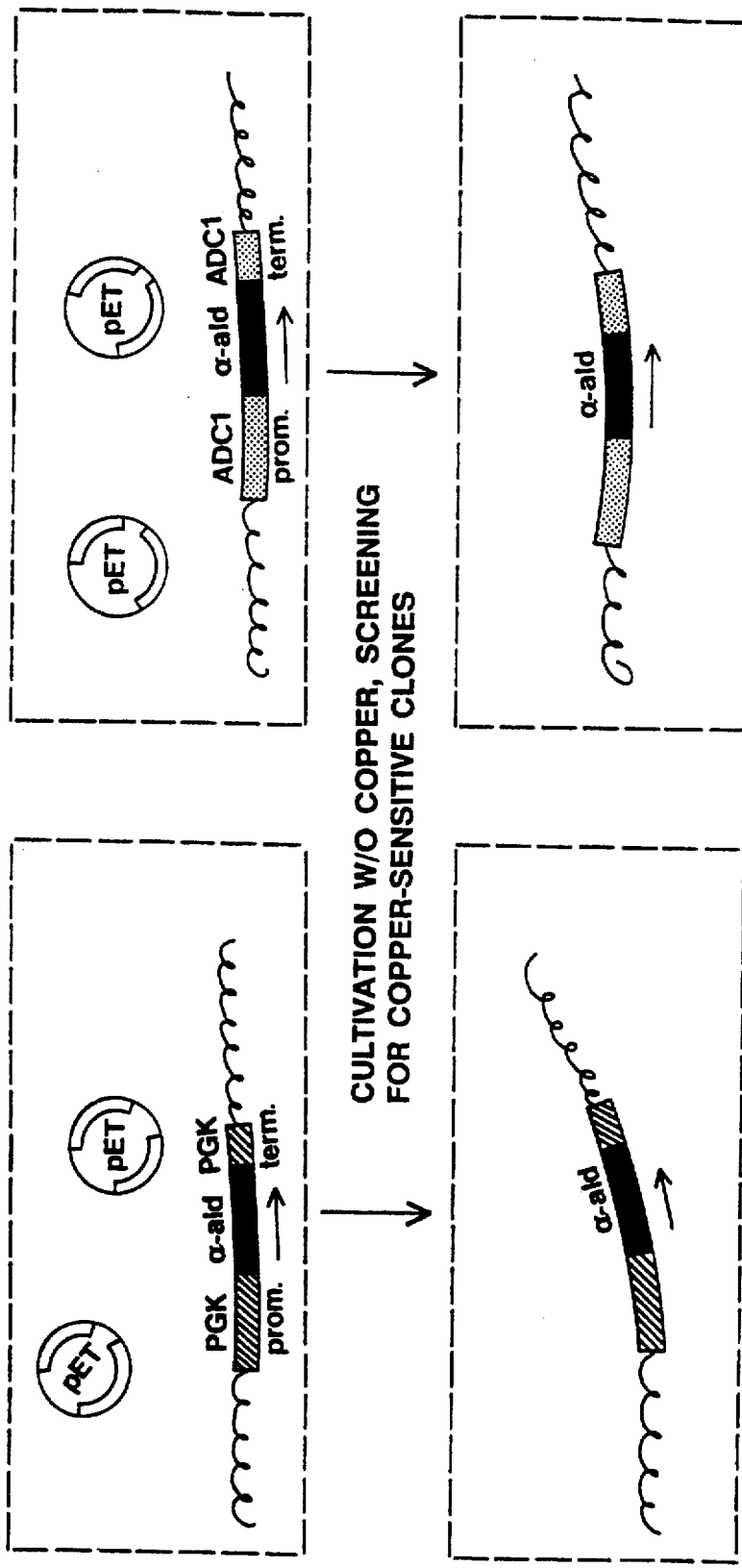
Figure 16A:
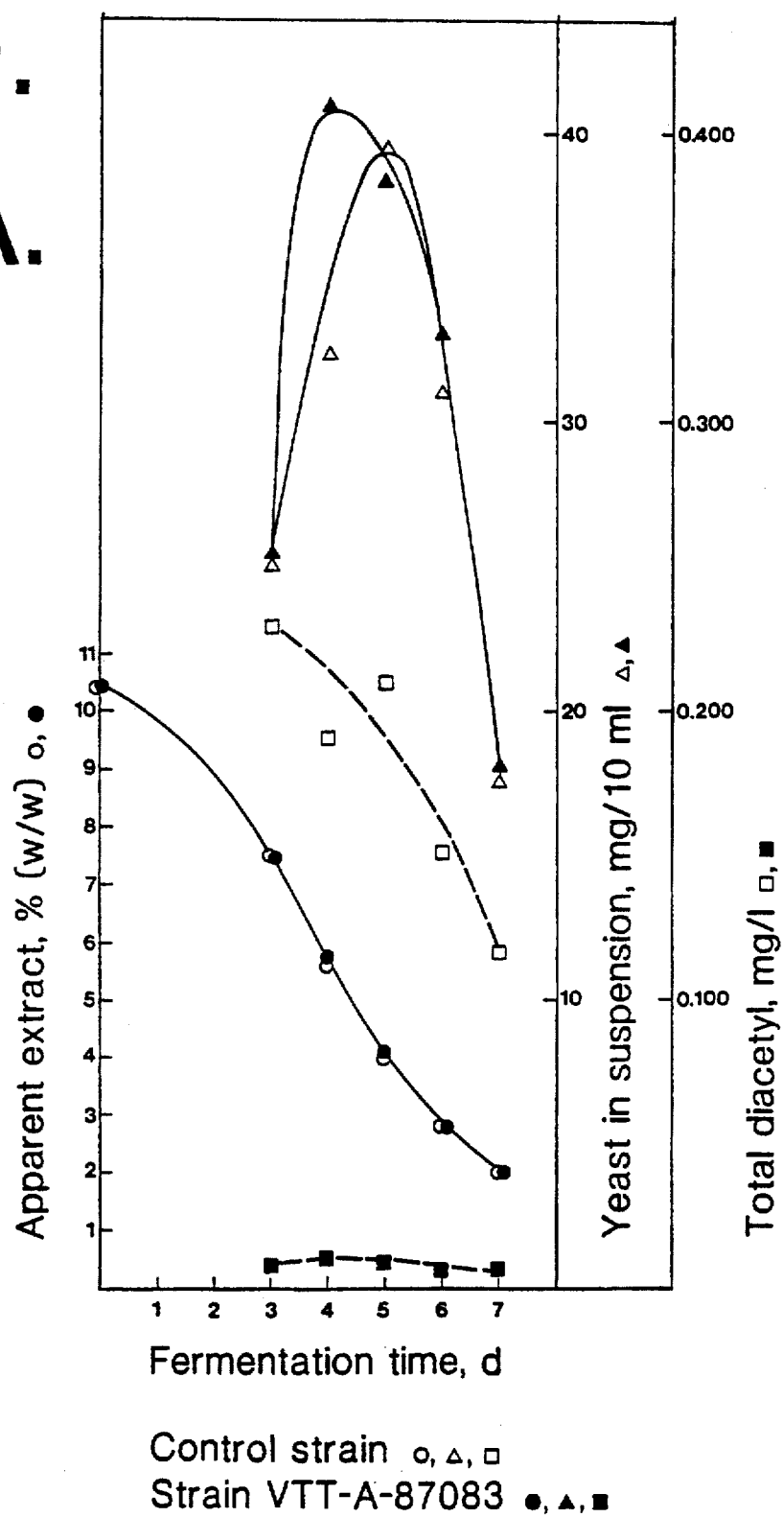
FIG. 16 (A-D) shows the brewing properties and formation of total diacetyl of the control strain VTT-A-63015 and the recombinant plasmid strains during the primary fermentation.
Figure 16B:
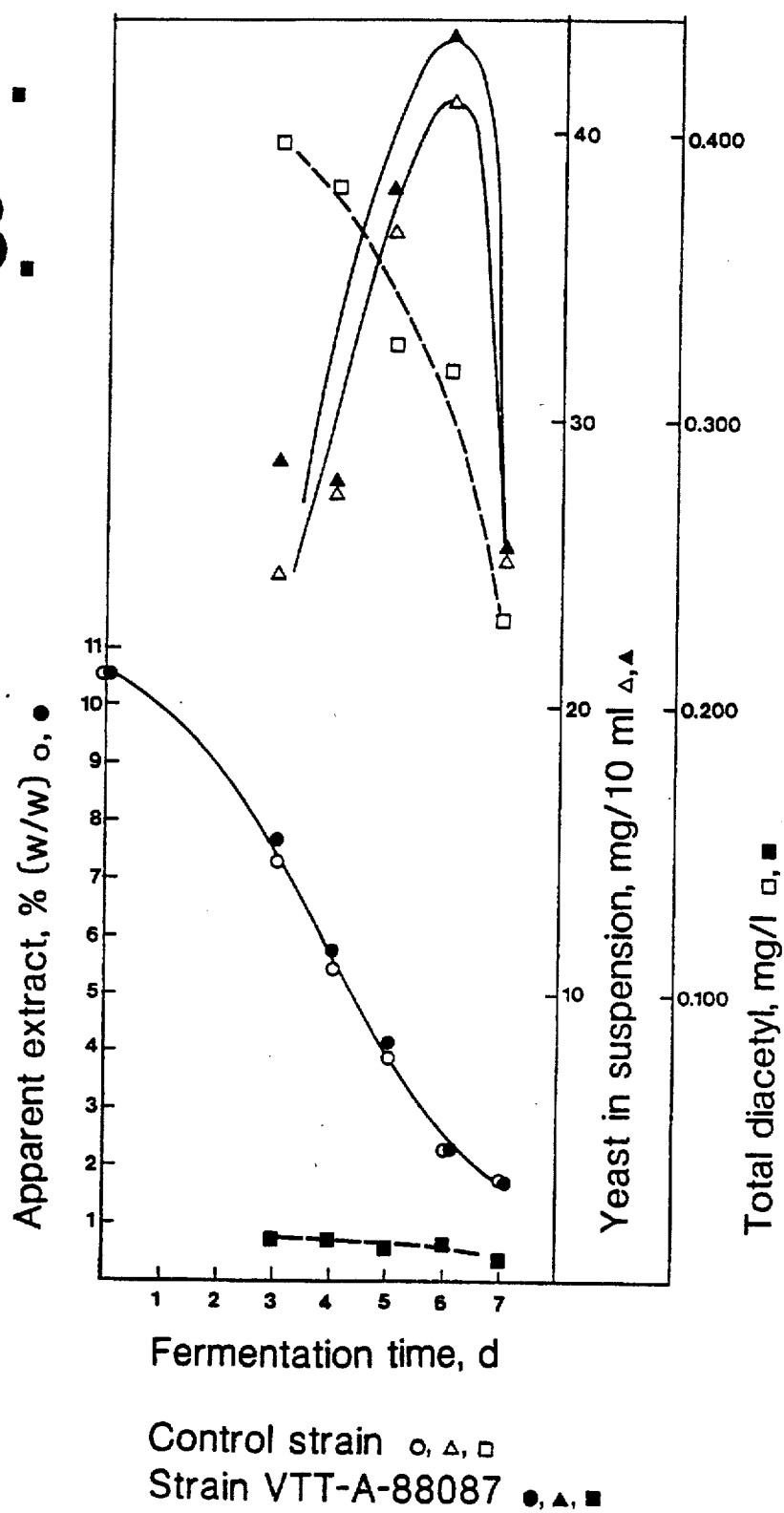
Figure 16C:
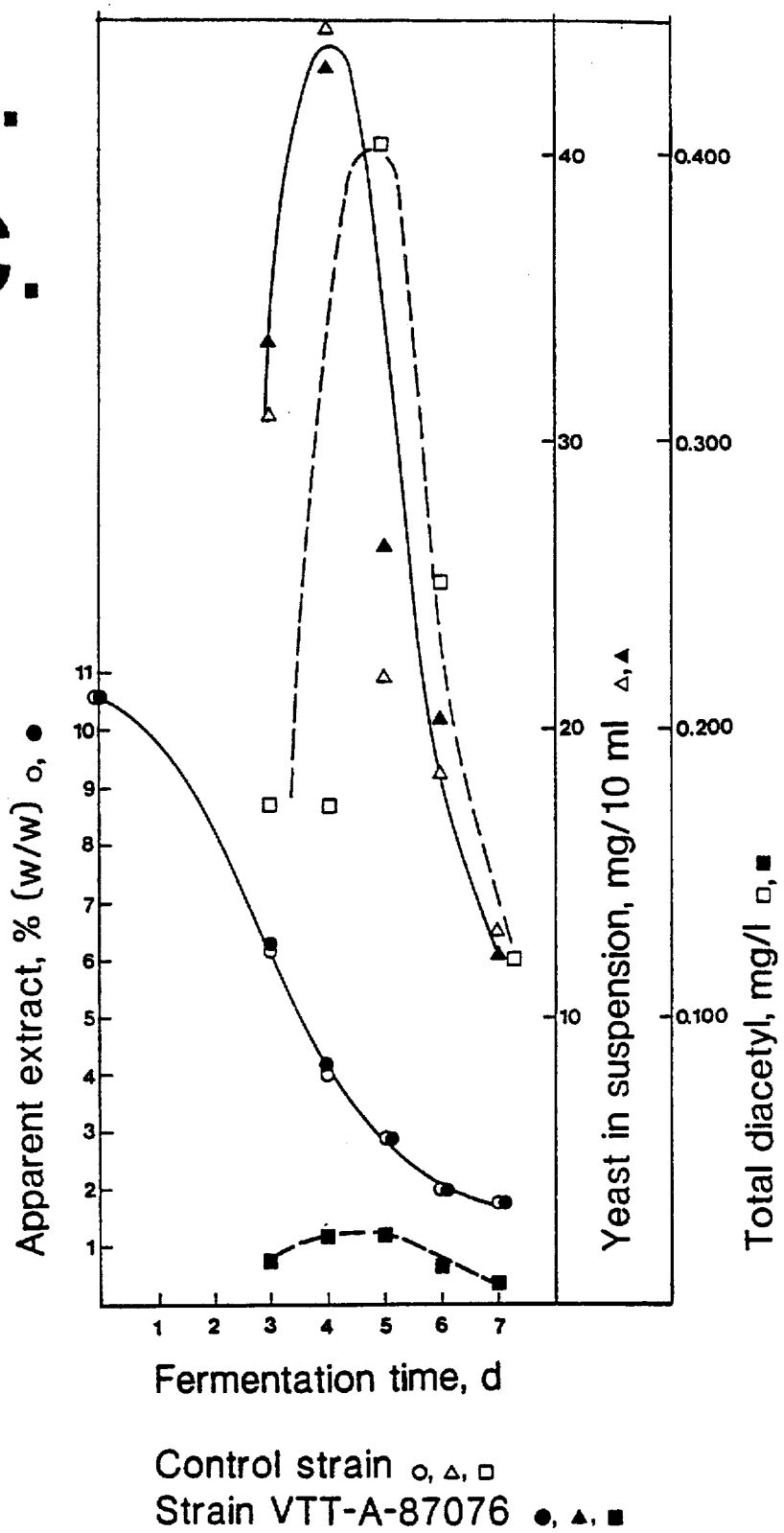
Figure 16D:
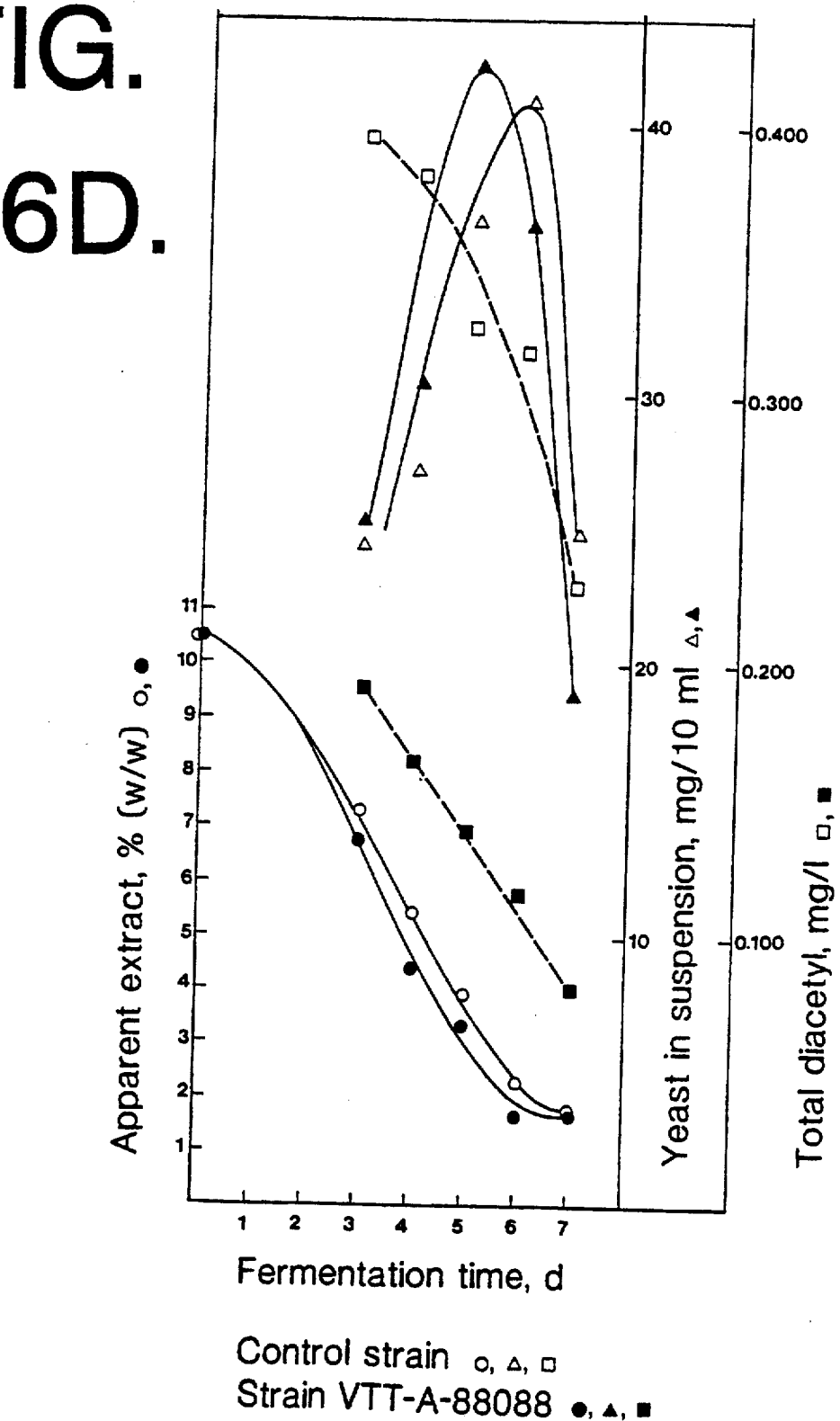
Figure 18A:
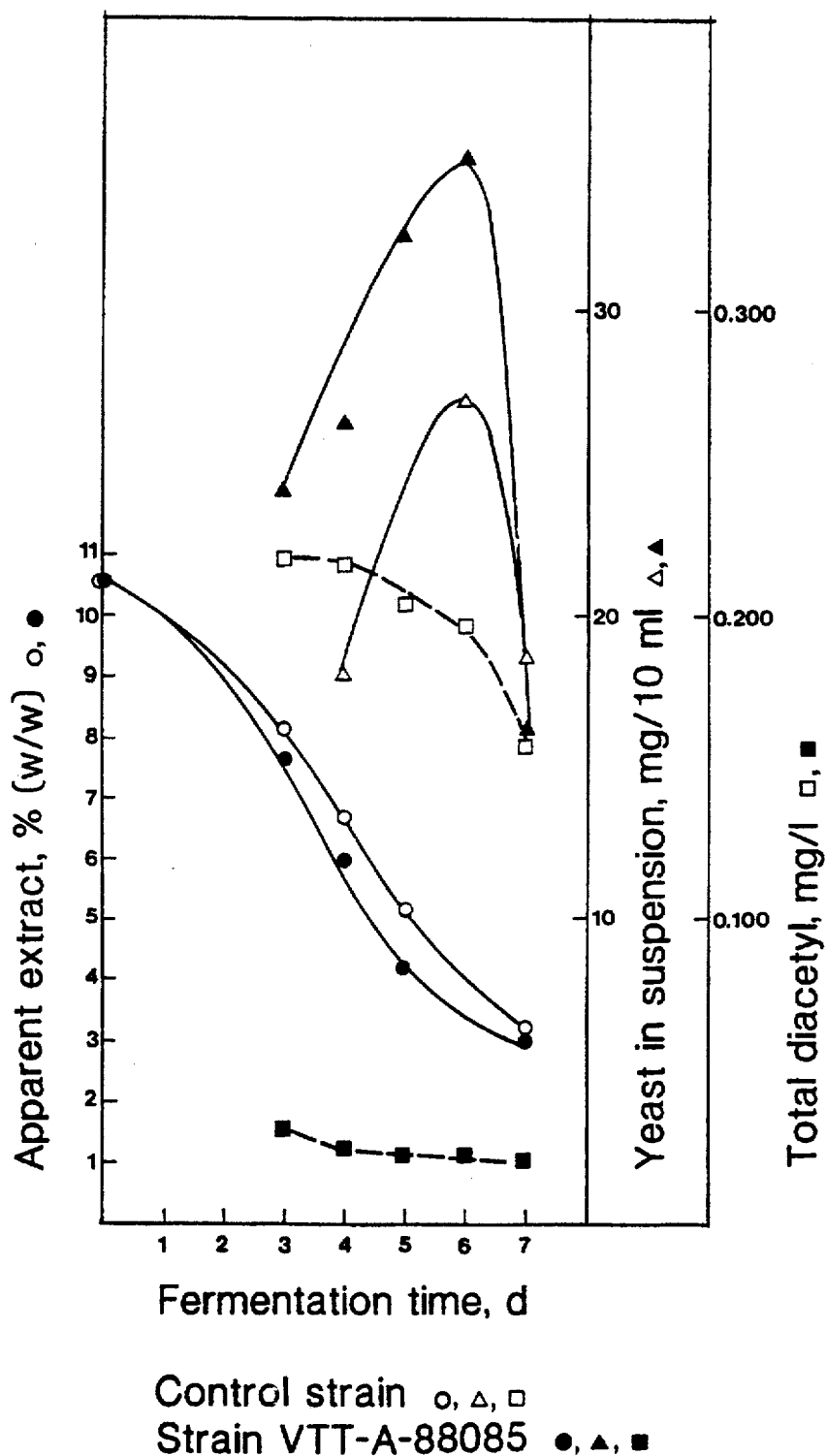
FIG. 18 (A-D) shows the brewing properties and formation of total diacetyl of the control strain VTT-A-63015 and the recombinant integrant strains during the primary fermentation.
Figure 18B:
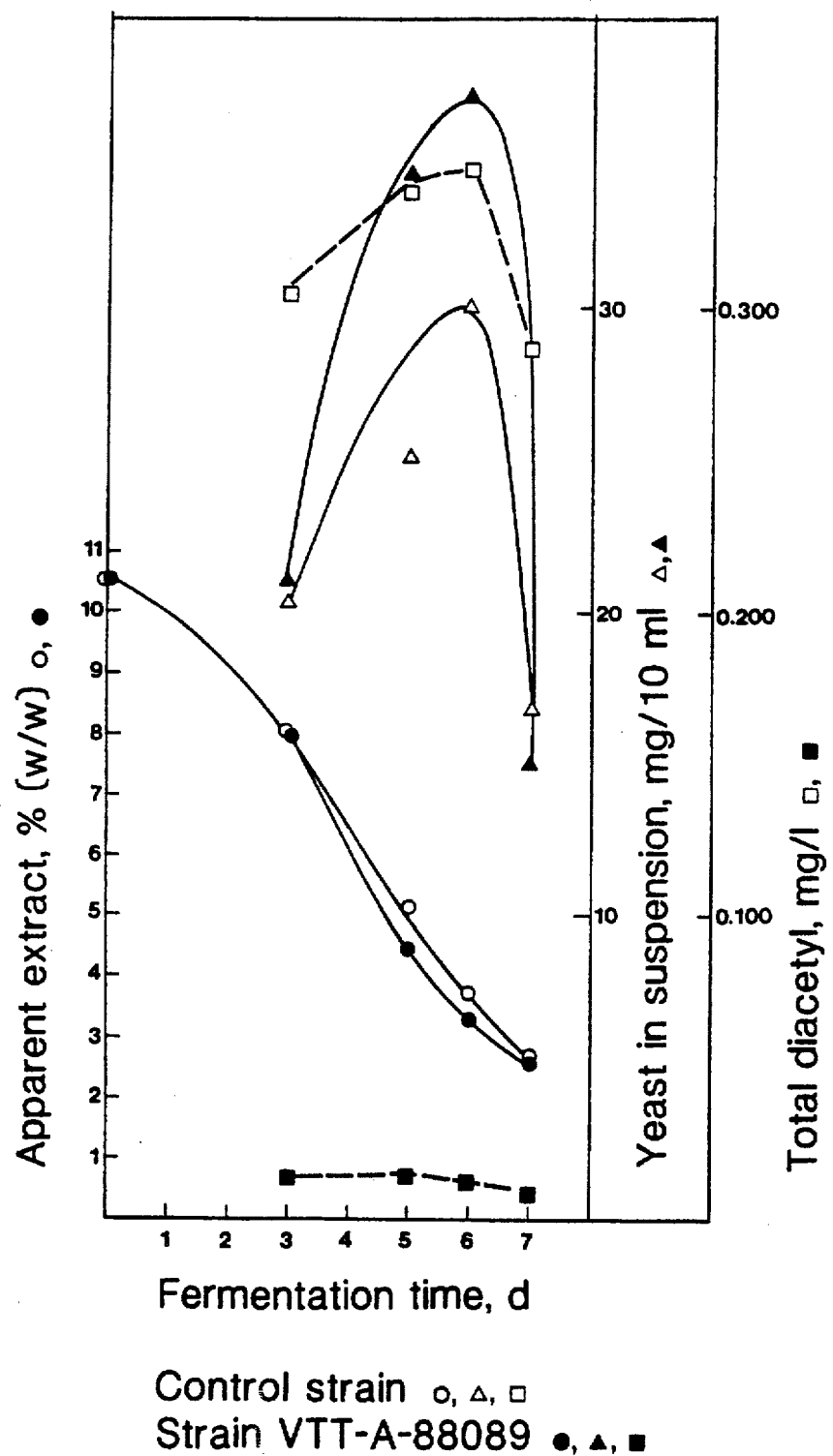
Figure 18C:
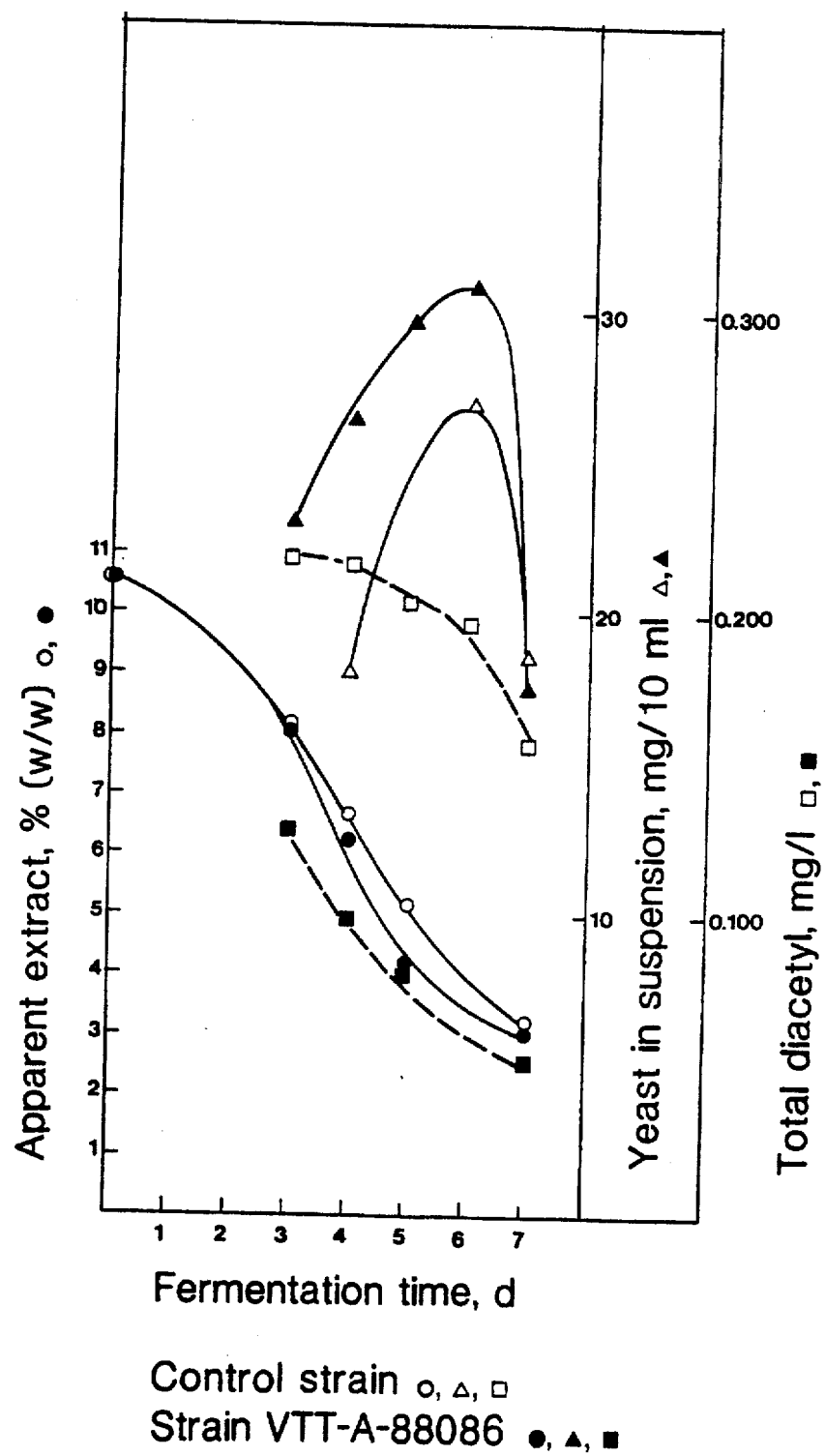
Figure 18D:
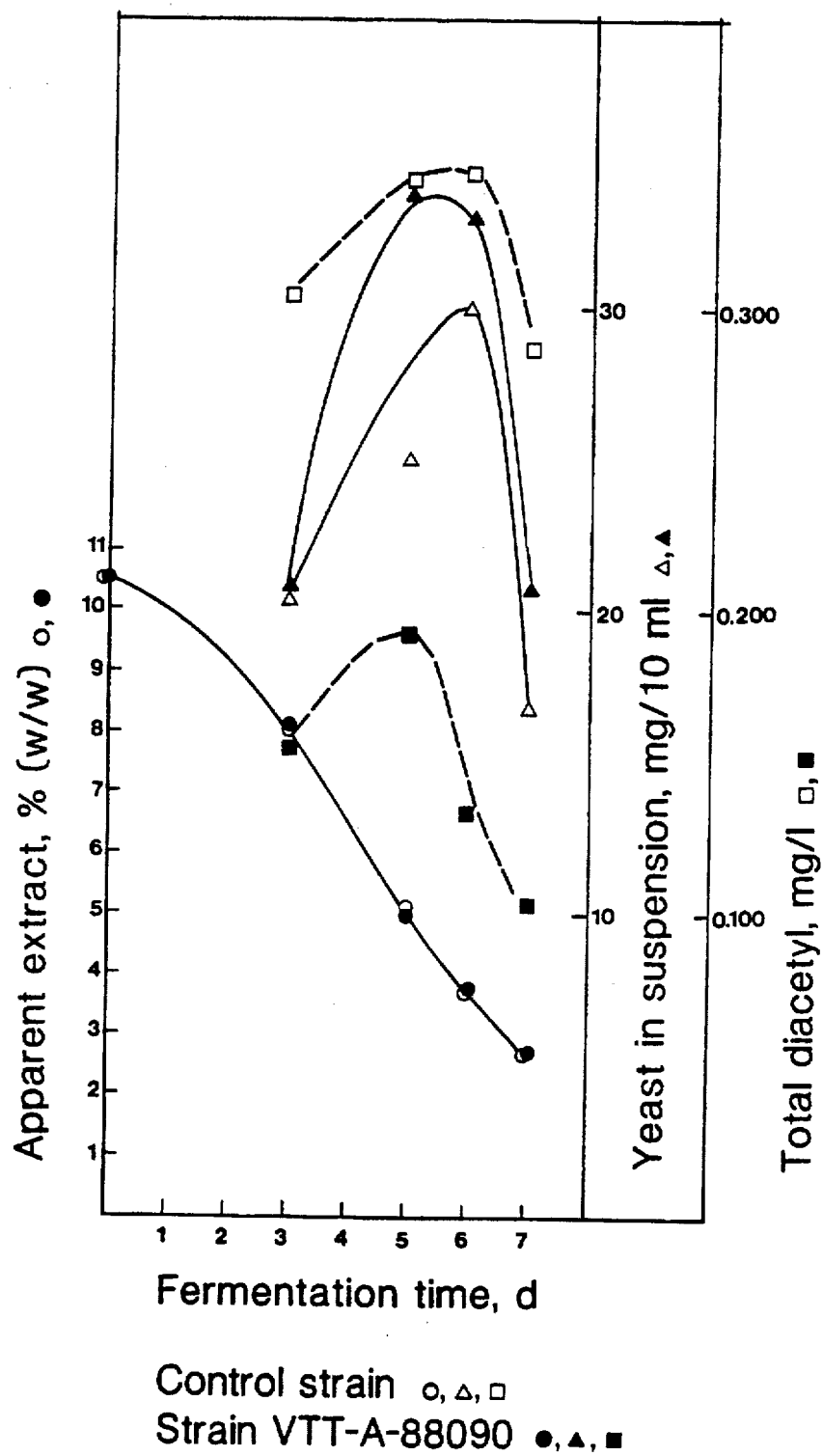

Co-transformation (FIG. 15) was used in the construction of the yeast strains. 5 μg of the PGK1/α-ald expression cassette isolated from the plasmid pKB007 (example 5), or the ADC1/α-ald cassette isolated from the plasmid pKB103 (example 5), which carried the α-ald gene of *A. aerogenes*, or the corresponding expression cassettes carrying the *E. aerogenes* gene (example 6), were transformed into the brewer's yeast strain VTT-A-63015 together with 5 μg of the plasmid pET13:1 using protoplast transformation (see methods). The transformants were selected on plates containing copper as described in example 7. Total DNA was isolated (see methods) from the transformants and the clones containing the α-ald gene were screened for by "dot blot" hybridization (see methods). To detect the *A. aerogenes* gene, a 0.95 kb long EcoRI-HindIII fragment isolated from the plasmid pKB101 (FIG. 4) was used as a probe, and to detect the *E. aerogenes* gene, the 0.9 kb long SalI-HindIII fragment isolated from the plasmid pPL4 (FIG. 7). The fragments were made radioactive with α-$^{32}$P-dCTP (Amersham, UK) using the "random primer labelling kit" (Boehringer Mannheim, FRG) according to the manufacturer's instructions. The α-ALDC activity of the transformants was tested from cell extracts using α-acetolactate as substrate (see methods).

The yeast clones containing the α-ald gene and showing α-ALDC activity were grown in YPD medium (no copper added) to remove the selection plasmid pET13:1. A single colony was grown in 10 ml of YPD for a day with shaking 250 rpm at 30°, and the cultivation was repeated by inoculating 10 ml of fresh YPD medium with 100 μl of the cells grown for a day. The cells from the second culture were plated onto YPD plates and the single colonies obtained were tested for copper sensitivity on plates containing 0.6 mM CuSO$_4$. Two to three percent of the clones tested were copper sensitive and had lost the plasmid pET13:1. The α-ALDC activity of these clones was analyzed and the presence of the α-ald gene verified by "dot blot hybridization" (see methods).

The yeast strain VTT-A-88085 and the strain VTT-A-88086, transformed with the PGK1/α-ald and the ADC1/α-ald expression cassettes, respectively, carried the α-ald gene of *A. aerogenes* and expressed α-ALDC activity, as did the corresponding strains VTT-A-88089 and VTT-A-88090 which contained the α-ald gene of *E. aerogenes*. These strains have the α-ald gene integrated to the yeast chromosome and contain no other foreign DNA. The strains have been deposited in VTT Collection of Industrial Microorganisms (Suihko, 1989). The strains VTT-A-88085 and VTT-A-88089 have been deposited also under the Budapest Treaty in DSM (Deutsche Sammlung von Mikroorganismen und Zellkulturen GmbH, Braunsweig, FRG) on Mar. 10, 1989. The deposition numbers are DSM 5233 and DSM 5234, respectively.

EXAMPLE 9

Production of beer with the plasmid strains

Yeast cells were inoculated from wort-sugar agar into 25 ml of wort-sugar solution and were incubated by shaking 200 rpm at 25° C. over night. 3 l of wort-sugar solution was inoculated with this culture and incubated by shaking 125 rpm at 25° C. for 2 days, the yeast cells were allowed to sediment for 2 days, the clear solution was decanted and the sedimented yeast mass sentrifuged. 125 g of this yeast mass was used for inoculation of a fermentation tube of 50 l.

Wort was obtained from a brewery and diluted to original gravity of 10.5%, w/w. The wort was aerated in keg vessels (à 50 l) using filtered press air 3 l/min for 30 min. Immediately after aeration the wort was removed using filtered press air to steely fermentation tubes (à 50 l) and inoculated with the yeast mass (2.5 g/l).

During the primary fermentation the temperature was 10° C. Fermentation was followed daily (3-7 d) by determining the amount of yeast in suspension (dry weight, mg/10 ml), apparent extract (specific gravity) and total diacetyl (free diacetyl and α-acetolactate). At the end of the primary fermentation alcohol content and yeast yield (the amount of sedimented yeast) were also determined. The young beer was removed to secondary fermentation at 10° C. or directly to stabilization for 3-5 days at 0° C. After that the beer was filtered (sheet filter + membrane), bottled and pasteurized for 30 min at 60° C. The finished beer was analyzed for apparent and real extract, apparent and real attenuation, original gravity, alcohol content, pH, colour, bitter substances, turbidity, chemical stability, foam stability, total VDK (vicinal dicetones and their precursors) and the main flavour compounds (ethyl acetate, isoamyl acetate, n-propanol, isobutanol, ethyl caproate, 3-methylbutanol or optically active amylalcohol, 2-methylbutanol or isoamylalcohol). The beer was also tested by the tasting panel (12-15 persons) and evaluated using the international flavour terms and scores from 5 to 1 (5=excellent, 4=good, 3=fairly good, 2=poor, 1=unacceptable).

The brewing properties and formation of total diacetyl during the primary fermentation with the control strain (VTT-A-63015) and recombinant plasmid strains are shown in FIGS. 16A-16D. The fermentation rate, yeast growth and flocculation were as good with all plasmid strains as with the control strain. The only difference was the formation of diacetyl. The formation of diacetyl with the strains VTT-A-87083 (A. aerogenes gene, PGK1 promoter) (FIG. 16A) and VTT-A-88087 (E. aerogenes gene, PGK1 promoter) (FIG. 16B) was less than the taste threshold value (0.020 mg/l) and no secondary fermentation was carried out. The maximal value of diacetyl of the strain VTT-A-87076 (A. aerogenes gene, ADC1 promoter) reached the threshold value (FIG. 16C), but at the end of the fermentation it was only 0.005 mg/l and no secondary fermentation was needed. Compared with other plasmid strains the formation of diacetyl with strain VTT-A-88088 (E. aerogenes gene, ADC1 promoter) (FIG. 16D) was high (max. 0.190 mg/l), but compared with the control strain (max. 0.395 mg/l) it was significantly lower. However, secondary fermentation of 4 days was needed, while the control strain needed 21 days. Also in this case the conventional production time was shortened significantly. The analysis of the finished beers are shown in FIG. 17. The quality of the trial beers was as good as that of the control beers.

EXAMPLE 10

Production of beer with the integrant strains

The beer was produced as described in example 9. The brewing properties and formation of total diacetyl during the primary fermentation with the control strain (VTT-A-63015) and the integrant strains are shown in FIGS. 18A-18D. The brewing properties were at least as good with all integrant strains as with the control strain. With the strains VTT-A-88085 (A. aerogenes gene, PGK1 promoter) (FIG. 18A) and VTT-A-88089 (E. aerogenes gene, PGK1 promoter) (FIG. 18B) the formation of diacetyl was so low (at the end of fermentation 0.020 mg/l and 0.010 mg/l, respectively) that no secondary fermentation was needed. The formation of diacetyl with the strains VTT-A-88086 (A. aerogenes gene, ADC1 promoter) (FIG. 18C) and VTT-A-88090 (E. aerogenes gene, ADC1 promoter) (FIG. 18D) was much higher, but less than with the control strain. For the beer produced with the strain VTT-A-88086 (diacetyl max. 0.130 mg/l, at the end 0.050 mg/l) secondary fermentation of 4 days was needed. Also for the beer produced with the strain VTT-A-88090 (diacetyl max. 0.190 mg/l, at the end 0.105 mg/l) secondary fermentation of 4 days was carried out but it was proved to be insufficient, the diacetyl was tasted in the beer. The secondary fermentation time of the control strain was in these cases 14 days, so the process was also with these strains shortened significantly. The analysis of the finished beers are shown in FIG. 19. The quality of the trial beers was as good as that of the control beers.

REFERENCES

Ammerer, G. 1983. Expression of genes in yeast using the ADC1-promoter. Methods Enzymol. 101, 192-210.

Amundsen, S. K. and Neville, M. E. 1979. Comparison of three procedures for isolating DNA from bacteria. Microbios 24, 29-39.

Analytica-EBC 1987. 4th ed. Brauerei-und Getränke-Rundschau, Zürich. 271 p.

Cantwell, B. A., Brazil, G., Murphy. N. and McConnell, D. J. 1986. Comparison of expression of the endo-β-1,2-1,4-glucanase gene from Bacillus subtilis in Saccharomyces cerevisiae from the CYC1 and ADH1 promoters. Curr. Genet. 11, 65-70.

Eghtedarzadeh, M. K. and Henikoff, S. 1986. Use of oligonucleotides to generate large deletions. Nucleic Acids Res. 14, 5115.

EP patent application 0128714. α-Acetolactate decarboxylase enzyme and preparation thereof. Novo Industri A/S.

Godtfredsen, S. E., Lorck, H. and Sigsgaard, P. 1983. On the occurrence of α-acetolactate decarboxylases among microorganisms. Carlsberg Res. Commun. 48, 239-247.

Godtfredsen, S. E. and Ottesen, M. 1982. Maturation of beer with α-acetolactate decarboxylase. Carlsberg Res. Commun. 47, 93-102.

Henderson, R. C. A., Cox, B. S. and Tubb, R. 1985. The transformation of brewing yeasts with a plasmid containing the gene for copper resistance. Curr. Genet. 9, 133-138.

Henikoff, S. 1984. Unidirectional digestion with exonuclease III creates targeted breakpoints for DNA sequencing. Gene 28, 351-359.

Hohn, B. and Murray, K. 1977. Packaging recombinant DNA molecules into bacteriophage particles in vitro. Proc. Natl. Acad. Sci. U.S.A. 74, 3259-3263.

Hollenberg, C. P. 1987. Construction of pentose-fermenting strains of Saccharomyces. EBC Symposium on Brewer's Yeast, Helsinki 1986, Monograph XII, 199-208.

Innis, M. A., Holland, M. J., McCabe, P. C., Cole, G. E., Wittman, V. P., Tal, R., Watt, K. W. K., Gelfand, D. H., Holland, J. P. and Meade, J. H. 1985. Expression, glycosylation and secretion of an Aspergillus glucoamylase by *Saccharomyces cerevisiae*. Science 228, 21-26.

Kingsman, S. M., Kingsman, A. J., Dobson, M. J., Mellor, J. and Roberts, N. A. 1985. Heterologous gene expression in *Saccharomyces cerevisiae*. Biotechnol. and Genet. Eng. Rev. 3, 377-415.

Knowles, J. K. C. and Tubb, R. 1987. Recombinant DNA: Gene transfer and expression techniques with industrial yeast strains. EBC Symposium on Brewer's Yeast, Helsinki 1986, Monograph XII, 169-185.

Krieg, N. R. and Holt, J. G. 1984. Bergey's Manual of Systematic Bacteriology, Vol. 1, Williams & Wilkins, Baltimore, 464.

Maniatis, T., Fritsch, E. F. and Sambrook, J. 1982. Molecular cloning: A laboratory manual. Cold Spring Harbor, U.S.A. 545 p.

Mellor, J., Dobson, M. J., Roberts, N. A., Tuite, M. F., Emtage, J. S., White, S., Lowe, P. A., Patel, T., Kingsman, A. J. and Kingsman, S. M. 1983. Efficient synthesis of enzymatically active calf chymosin in *Saccharomyces cerevisiae*. Gene 24, 1-14.

Pajunen, E., Mäkinen, V. and Gisler, R. 1987. Secondary fermentation with immobilized yeast. Proc. 21st EBC Congress, Madrid 1987, 441-448.

Penttilä, M. E., Nevalainen, K. M. H., Raynal, A. and Knowles, J. K. C. 1984. Cloning of *Aspergillus niger* genes in yeast. Expression of the gene coding Aspergillus beta-glucosidase. Mol. Gen. Genet. 114, 494-499.

Penttilä, M. E., Suihko, M. -L., Lehtinen, U., Nikkola, M. and Knowles, J. K. C. 1987. Construction of brewer's yeasts secreting fungal endo-$\beta$-glucanase. Curr. Genet. 12, 413-420.

Sanger, F., Niclen, S. and Coulson, A. R. 1977. DNA-sequencing with chain-terminating inhibitors. Proc. Natl. Acad. Sci. U.S.A. 74, 5463-5467.

So, M., Boyer, H., Betlach, M. and Fallow, S. 1978. Molecular cloning of an *Escherichia coli* plasmid determinant that encodes for the production of heat-stable enterotoxin. J. Bacteriol. 128, 463.

Sone, H., Fujii, T., Kondo, K. and Tanaka, J. -I. 1987. Molecular cloning of the gene encoding $\alpha$-acetolactate decarboxylase from *Enterobacter aerogenes*. J. Biotechnol. 5, 87-91.

Stepien, D. P., Brousseau, R., Wu, R., Narang, S. and Thomas, D. Y. 1983. Synthesis of a human insulin gene. VI. Expression of the synthetic proinsulin gene in yeast. Gene 24, 289-297.

Suihko, M. -L. 1989, VTT Collection of Industrial Microorganisms, Catalogue of strains, 2nd ed., Espoo, in press.

Urdea, M. S., Merryweather, J. P., Mullenbach, D. C., Coit, D., Heberlein, U., Valenzuela, P. and Barr, P. J. 1983. Chemical synthesis of a gene for human epidermal growth factor urogastrone and its exression in yeast. Proc. Natl. Acad. Sci. U.S.A. 80, 7461-7465.

Yanisch-Perron, C., Vieira, J. and Messing. J. 1985. Improved M13 phage cloning vectors and host strains: nucleotide sequences of the M13mp18 and pUC19 vectors. Gene 33, 103-119.

Yocum, R. R. 1986. Genetic engineering of industrial yeasts. Proceedings Bio Expo 86, Butterworth, Stoneham Mass., 171-180.

Zagursky, R. J., Berman, M. L., Baumeister, K. and Lomax, N. 1986. Rapid and easy sequencing of large linear double stranded DNA and supercoiled plasmid DNA. Gene Anal. Techn. 2, 89-94.

We claim:

1. A process for accelerated beer production, which comprises:
   brewing beer with a *Saccharomyces cerevisiae* brewer's yeast strain having a gene coding for the enzyme $\alpha$-acetolactate decarboxylase ($\alpha$-ALDC) (EC 4.1.1.5) inserted into the ADC1 or PGK1 gene locus thereof.

2. The process of claim 1, wherein said gene coding for the enzyme $\alpha$-ALDC is inserted into the ADC1 gene locus and is coupled to regulatory regions of the ADC1 gene.

3. The process of claim 1, wherein said gene coding for the enzyme $\alpha$-ALDC is inserted into the PGK1 gene locus and is coupled to regulatory regions of the PGK1 gene.

4. The process of claim 1, wherein the gene coding for the enzyme $\alpha$-ALCD is endogenous to a bacterial strain selected from the group consisting of *Aerobacter aerogenes* and *Enterobacter aerogenes*.

5. The process of claim 4, wherein the ACD1 or PGK1 gene locus is replaced by using an expression cassette and homologous recombination techniques.

6. The process of claim 1, wherein no secondary fermentation is carried out.

7. The process of claim 6, wherein said yeast strain is *Saccharomyces cerevisiae* VTT-A-880885 or *Saccharomyces cerevisiae* VTT-A-88089.

8. The process of claim 1, wherein secondary fermentation of no more than 4 days is carried out.

9. A *Saccharomyces cerevisiae* yeast strain having a gene coding for the enzyme $\alpha$-acetolactate decarboxylase ($\alpha$-ALDC) (EC 4.1.1.5) inserted into the ADC1 or PGK1 gene locus thereof.

10. The *Saccharomyces cerevisiae* yeast strain of claim 9, wherein said gene coding for the enzyme $\alpha$-ALDC is coupled to regulatory regions of the yeast's ADC1 gene.

11. The *Saccharomyces cerevisiae* yeast strain of claim 9, wherein said gene coding for the enzyme $\alpha$-ALDC is coupled to regulatory regions of the yeast's PGK1 gene.

12. The *Saccharomyces cerevisiae* of claim 10, wherein said regulatory regions are an ADC1 promoter and ADC1 terminator.

13. The *Saccharomyces cerevisiae* of claim 11, wherein said regulatory regions are an PGK1 promoter and PGK1 terminator.

14. The *Saccharomyces cerevisiae* of claim 9, wherein there is no foreign DNA, other than that of the $\alpha$-ALDC1 gene, inserted into said gene locus.

15. The *Saccharomyces cerevisiae* of claim 9, which is *Saccharomyces cerevisiae* VTT-A-88085.

16. The *Saccharomyces cerevisiae* of claim 9, which is *Saccharomyces cerevisiae* VTT-A-88089.

* * * * *

UNITED STATES PATENT AND TRADEMARK OFFICE
CERTIFICATE OF CORRECTION

PATENT NO. :  5,108,925
DATED      :  Apr. 28, 1992
INVENTOR(S):  Enari et al.

It is certified that error appears in the above-identified patent and that said Letters Patent is hereby corrected as shown below:

On the Title page, item [75] Inventors:

Change "Maija-Liisa A. Suthko" to --Maija-Liisa A. Suihko--,

After "Merja E. Penttila" insert --Jonathan K.C. KNOWLES--,

Change "both of Helsinki" to -- all of Finland--.

Signed and Sealed this

Twentieth Day of July, 1993

Attest:

MICHAEL K. KIRK

*Attesting Officer*    Acting Commissioner of Patents and Trademarks